US007479579B2

(12) United States Patent
LaFerla

(10) Patent No.: US 7,479,579 B2
(45) Date of Patent: Jan. 20, 2009

(54) TRIPLE TRANSGENIC MOUSE MODEL OF ALZHEIMER'S DISEASE

(75) Inventor: Frank M. LaFerla, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 258 days.

(21) Appl. No.: 10/499,269

(22) PCT Filed: Dec. 20, 2002

(86) PCT No.: PCT/US02/40929

§ 371 (c)(1),
(2), (4) Date: Sep. 8, 2004

(87) PCT Pub. No.: WO03/053136

PCT Pub. Date: Jul. 3, 2003

(65) Prior Publication Data

US 2005/0022256 A1 Jan. 27, 2005

Related U.S. Application Data

(60) Provisional application No. 60/343,383, filed on Dec. 20, 2001.

(51) Int. Cl.
G01N 33/00 (2006.01)
A01K 67/033 (2006.01)
C12N 15/00 (2006.01)

(52) U.S. Cl. .................. 800/12; 800/3; 800/12; 800/22

(58) Field of Classification Search ............. 800/12–18, 800/3, 25
See application file for complete search history.

(56) References Cited

U.S. PATENT DOCUMENTS

| 5,877,399 | A * | 3/1999 | Hsiao et al. .................... 800/3 |
| 6,245,964 | B1 | 6/2001 | McLonlogue et al. |
| 6,262,335 | B1 | 7/2001 | Hsiao et al. |
| 6,395,960 | B1 | 5/2002 | St. George-Hyslop et al. |
| 6,475,723 | B2 | 11/2002 | Hutton et al. |
| 6,509,515 | B2 | 1/2003 | Hsiao et al. |
| 6,664,443 | B1 | 12/2003 | Hutton et al. |

OTHER PUBLICATIONS

Fisher et al. M1 Agonists of the Treatment of Alzheimer's Disease. Novel Properties and Clinical Update. Annals of the New York Academy of Sciences. 1996,vol. 777, pp. 189-196.*
Patel et al. Identification of Immunodominant .T Cell Epitopes of Human Glutamic Acid Decarboxylase 65 by Using HLA-DR (Alpha1*0101, Beta1*0401) Transgenic Mice. Proc. Natl. Acad. Sci., vol. 94, pp. 8082-8087.*
Lamb et al. Amyloid production and Deposition in Mutant Amyloid Precursor Protein and Presenilin-1 Yeast Artifical Chromosome Transgenic Mice. Nature Neuroscience. Aug. 1999, vol. 2, No. 8, pp. 695-697, yn.*
McGowan et al. Amyloid Phenotype Characterization of Transgenic Mice Overexpressing both Mutant Amyloid Precursor Protein and Mutant Presenilin-1. Neurobiology of Disease. 1999, vol. 6, 231-244.*
Lewis et al. Neurofibriallary Tangles, Amyotrophy and Progressive Motor Disturbance in Mice Expressing Mutant (P301L) Tau Protein. Nature Genetics. Aug. 2000, vol. 25, pp. 402-405.*
Guo et al. Increased Vunerability of Hippocampal Neurons to Excitoxic Necrosis in Presenilin-1 Mutant Knock-In Mice. Nature Medicine. Jan. 1999, vol. 5, pp. 101-106.*
Bornemann et al. Transgenic Mouse Models of Alzheimer's Disease. Annals New York Acad. Sci. 2000, vol. 908, pp. 260-266.*
Echeverria et al. Rat Transgenic Models with Phenotype of Intracellular A-Beta Accumulation in Hippocampus and Cortex. J.Alzheimer's Disease. 2004, vol. 6, pp. 209-219.*
Dudal et al. Inflammation Occurs Early During the A-Beta Deposition Process in TgCRND8 Mice. Neurobiol. Aging. 2004, vol. 25, pp. 861-871.*
Citron et al. Mutant Presenilins of Alzheimer's Disease Increase Production of 42-Residue Amyloid Beta Protein in both Transfected Cells and Transgenic Mice. Nature Med. Jan. 1997, vol. 3, No. 1, pp. 67-72.*
Smith. Gene Transfer in Higher Animals: Theoretical Considerations and Key Concepts. J. Biotech. 2002, vol. 99, pp. 1-22.*
Wheeler, M. B. et al. Transgenic Technology and Applications in Swine. Theriogenelogy. 2001, vol. 56, pp. 1345-1369.*
Prelle, K. et al. Establishment of Pluripotent Cell Lines from Vertebrate Species—Present Status and Future Prospects. Cells Tissues Organs. 1999, vol. 165, pp. 220-236.*
Moreadith, R. W. Gene Targeting in Embryonic Stem Cells: the New Physiology and Metabolism. J. Molecular Med. 1997, vol. 75, pp. 208-216.*
Finckh et al. HIgh Frequency of Mutations in Four Different Disease Genes in Early-Onset Dementia. Annals of the New York Academy of Sciences. 2000, vol. 920 (Molec. Basis of Dementia), pp. 100-106.*
Hutton, M. Molecular Genetics of Chromosome 17 Tauopathies. Annals of the New York Academy of Sciences. 2000, vol. 920 (Molec. Basis of Dementia), pp. 63-73.*
Chapman et al., "Impaired Synaptic Plasticity and Learning In Aged Amyloid Precursor Protein Transgenic Mice", Nature Neuroscience, vol. 2, No. 3, Mar. 1999, pp. 271-276.
Dekosky et al., "Synapse Loss in Frontal Cortex Biopsies in Alzheimer's Disease: Correlation with Cognitive Severity", Annals of Neurology, vol. 27, No. 5, May 1990, pp. 457-464.

(Continued)

Primary Examiner—Deborah Crouch
(74) Attorney, Agent, or Firm—Kauth, Pomeroy, Peck & Bailey LLP

(57) ABSTRACT

The present invention relates to a triple transgenic animal model for Alzheimer's disease as well as to methods for generating multi-transgenic animals. The present invention also relates to methods for screening biologically active agents potentially useful for treating and/or ameliorating Alzheimer's disease (AD) or AD-type pathologies, compositions useful for treating AD or AD-type pathologies, and methods of treating AD patients.

46 Claims, 16 Drawing Sheets

OTHER PUBLICATIONS

Dickson et al., "Correlations of Synaptic and Pathological Markers With Cognition of the Elderly", Neurobiology of Aging, vol. 16, No. 3, 1995, pp. 285-298.

Fitzjohn et al., "Age-Related Impairment of Synaptic Transmission But Normal Long-Term Potentiation in Transgenic Mice that Overexpress the Human APP695SWE Mutant Form of Amyloid Precursor Protein", The Journal of Neuroscience, vol. 21, No. 13, Jul. 1, 2001, pp. 4691-4698.

Hsia et al., "Plaque-Independent Disruption of Neural Circuits in Alzheimer's Disease Mouse Models", Proc. Natl. Acad. Sci. USA, vol. 96, Mar. 1999, pp. 3228-3233.

Larson et al., "Alterations in Synaptic Transmission and Long-Term Potentiation in Hippocampal Slices from Young and Aged PDAPP Mice", Brian Research, vol. 840, 1999, pp. 23-35.

Masliah et al., "Altered Expression of Synaptic Proteins Occurs Early During the Progression of Alzheimer's Disease", Neurology, vol. 56, Jan. (1 of 2) 2001, pp. 127-129.

Scheff et al., "Quantitation of Synaptic Density in the Septal Nuclei of Young and Aged Fischer 344 Rats", Neurobiology of Aging, vol. 12, 1991, pp. 3-12.

Selkoe, Dennis, "Alzheimer's Disease Is A Synaptic Failure", Science, vol. 298, Oct. 25, 2002, pp. 789-791.

Selkoe, Dennis, "Alzheimer's Disease: Genes, Proteins and Therapy", Physiological Reviews, vol. 81, No. 2, Apr. 2001, pp. 741-766.

Sze et al., "Loss of the Presynaptic Vesicle Protein Synaptophysin In Hippocampus Correlates with Cognitive Decline in Alzheimer Disease", Journal of Neuropathology and Experimental Neurology, vol. 56, No. 8, Aug. 1997, pp. 933-944.

Terry et al., "Physical Basis of Cognitive Alterations in Alzheimer's Disease: Synapse Loss Is The Major Correlate of Cognitive Impairment", Annals of Neurology, vol. 30, No. 4, Oct. 1991, pp. 572-580.

Wong et al., "Genetically Engineered Mouse Models of Neurodegenerative Diseases", Nature Neuroscience, vol. 5, No. 7, Jul. 2002, pp. 633-639.

Oddo et al., "Triple Transgenic Model of Alzheimer's Disease with Plaques and Tangles: Intracellular Aβ and Synaptic Dysfunction," Neuron, vol. 39(3), pp. 409-421 (Jul. 31, 2003).

Schenk et al., "Immunization with Amyloid-β Attenuates Alzheimer-Disease-Like Pathology in the PDAPP Mouse," Nature, vol. 400, pp. 173-177 (Jul. 8, 1999).

Laub et al., "Replacement of Murine by Human CD4 and Introduction of HLA-DR17 in Mice: A Triple-Transgenic Animal Model to Study Human MHC II-CD4 Interaction In Situ*," Journal of Experimental Animal Science, vol. 39, pp. 122-135, (1998/99).

Haute et al., "Coexpression of Human CDK5 and its Activator P35 with Human Protein Tau in Neurons in Brain of Triple Transgenic Mice," Neurobiology of Disease, vol. 8, pp. 32-44 (2001).

Simon et al., "The Lack of NF-$_K$b Transactivation and PKCε Expression In CD4$^+$CD8$^+$Thymocytes Correlates with Negative Selection," Cell Death and Differentiation vol. 7, pp. 1253-1262 (2000).

Dewachter et al. "Modeling Alzheimer's Disease in Transgenic Mice: Effect of Age and of Presenilin 1 on Amyloid Biochemistry and Pathology in APP/London Mice," Experimental Gerontology, vol. 35, pp. 831-841 (2000).

Takeuchi et al., "Age-Related Amyloid β Deposition in Transgenic Mice Overexpressing Both Alzheimer Mutant Presenilin 1 and Amyloid β Precursor Protein Swedish Mutant is Not Associated with Global Neuronal Loss," American Journal of Pathology, vol. 157, No. 1, pp. 331-339 (Jul. 2000).

Dorpe et al., "Prominent Cerebral Amyloid Angiopathy in Transgenic Mice Overexpressing the London Mutant of Human APP In Neurons," American Journal of Pathology, vol. 157, No. 4, pp. 1283-1298 (Oct. 2000).

Wengenack et al., "Quantitative Histological Analysis of Amyloid Deposition In Alzheimer's Double Transgenic Mouse Brain," Neuroscience, vol. 101, No. 4, pp. 939-944 (2000).

Leuven, "Single and Multiple Transgenic Mice as Models for Alzheimer's Disease," Neurobiology, vol. 61, pp. 305-312 (2000).

Wong et al., "Reorganization of Cholinergic Terminals in the Cerebral Cortex and Hippocampus in Transgenic Mice Carry Mutated Presenilin-1 and Amyloid Precursor Protein Transgenes," The Journal of Neuroscience, vol. 19(7), pp. 2706-2716 (Apr. 1, 1999).

Götz et al., "In Vivo Analysis Of Wild-Type And FTDP-17 Tau Transgenic Mice," Annals of the New York Academy of Sciences, vol. 920, pp. 126-133 (2000).

Duff et al., "Characterization of Pathology in Transgenic Mice Over-Expressing Human Genomic and cDNA Tau Transgenes," Neurobiology of Disease, vol. 7, pp. 87-98 (2000).

\* cited by examiner

FOUNDER LINES

|     | PS1$_{M146V}$ KI | APP$_{sw}$ | Tau$_{P301L}$ |
|-----|------------------|------------|---------------|
| A1  | +/+              | -/0        | +/0           |
| A2  | +/+              | +/0        | +/0           |
| B1  | +/+              | +/0        | +/0           |
| F5  | +/+              | +/0        | +/0           |
| F7  | +/+              | +/0        | +/0           |
| G6  | +/+              | +/0        | +/0           |

*Advantages*

Breed as if they were a "single" transgenic strain
-facilitates breeding
-reduces genetic screening process
-reduces time required to establish large mouse colony Offspring are genetically homogenous —an important criteria for behavioral, biochemical, & immunological studies

FIG. 2

| | Aβ Elisa | | |
| --- | --- | --- | --- |
| | Aβ 40 | Aβ42 | 42/40 |
| | (pmol/g tissue wet weight) | | |
| B1 (4 month) | 14.81 | 58.61 | 3.96 |
| Tg2576 (6 mo) | 94.85 | >150 | 1.58 |

10% Bis Tris western-blot showing Aβ (6 Kd) in a 4.5 month-old T13B1 mice. Primary antibody 6E10 (1:500)

| NAME | DOB | SEX | Comment |
|---|---|---|---|
| YA3 | 06.17.01 | M | 19/19 positive |
| YB1 | 07.03.01 | F | 8/8 positive |
| YB4 | 07.03.01 | M | 18/18 positive |
| B1(B2B5)A1 | 06.06.01 | F | 10/10 positive |
| B1(B2B5)A4 | 06.06.01 | M | 16/16 positive |
| B1(B2B5)A5 | 06.06.01 | M | 5/5 positive |
| B1(G3G4)A2 | 06.25.01 | F | 7/7 positive |
| B1(G3G4)B1 | 07.17.01 | F | 19/19 positive |
| B1(G3G4)B3 | 07.17.01 | F | Still breeding |
| B1(G3G4)B6 | 07.17.01 | F | 15/15 positive |
| B1(G3G4)B7 | 07.17.01 | M | 18/18 positive |
| B1(G3G4)B8 | 07.17.01 | M | 10/10 positive |
| B1(G3G4)B9 | 07.17.01 | M | 14/14 positive |
| B1(D1D3)A2 | 06.25.01 | M | 10/10 positive |
| B1(D1D3)A3 | 06.25.01 | M | 5/5 positive |

| NAME | DOB | SEX | Comment |
|---|---|---|---|
| A1(B5B6)B5 | 05.29.01 | M | 17/17 positive |
| A1(B5B6)B6 | 05.29.01 | F | 14/14 positive |

FIG. 7

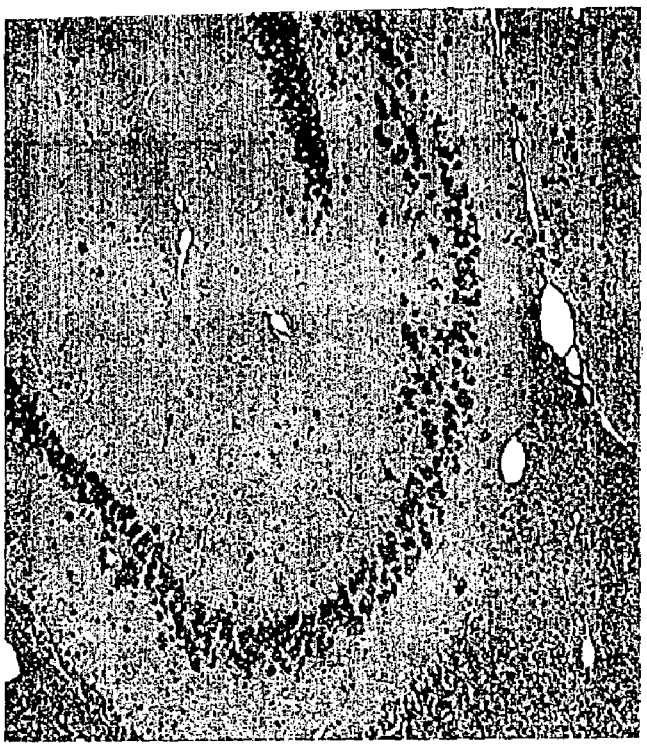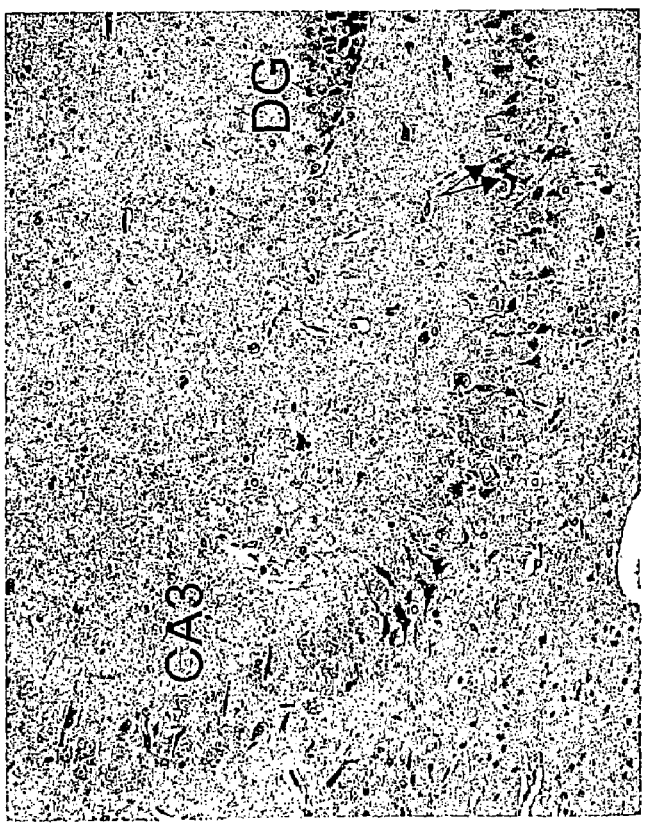
FIG. 9

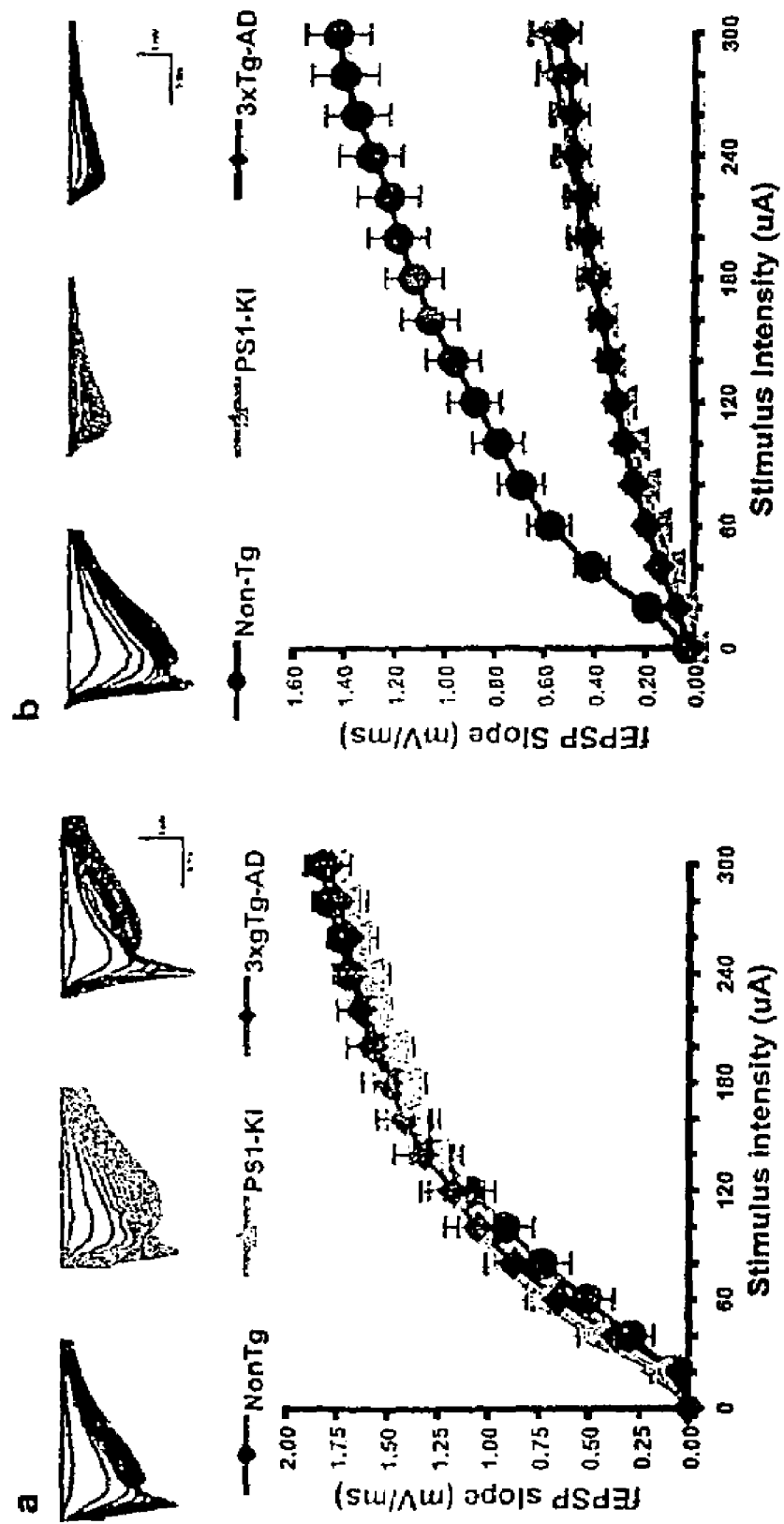
FIG. 14A, B

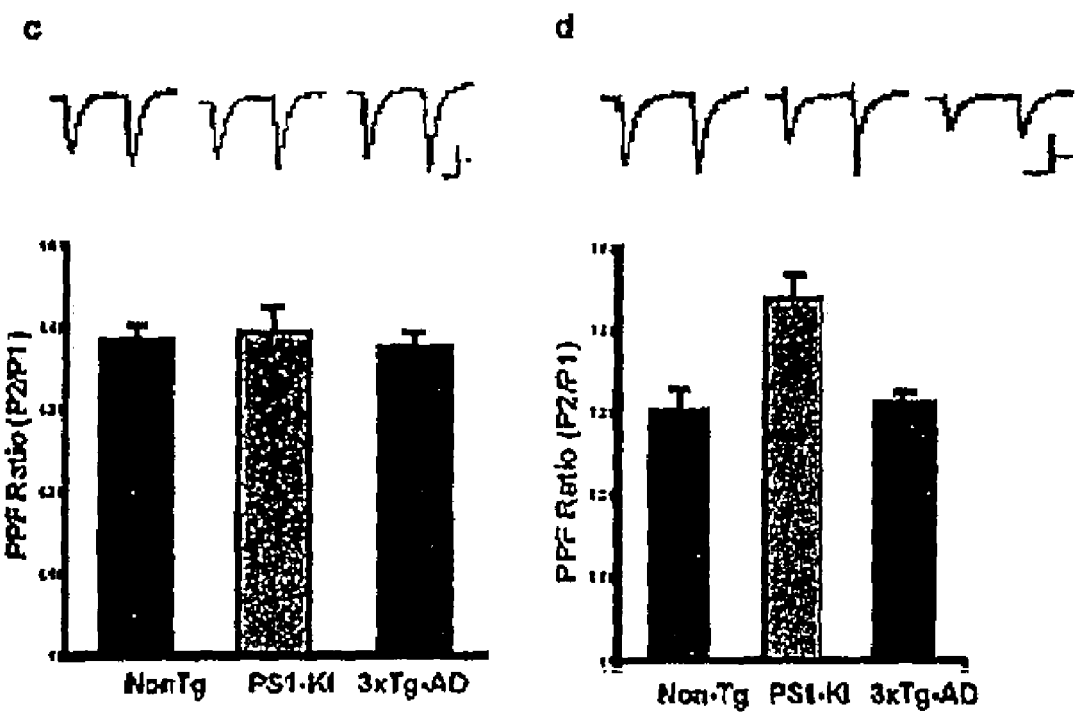
FIG. 14 C,D

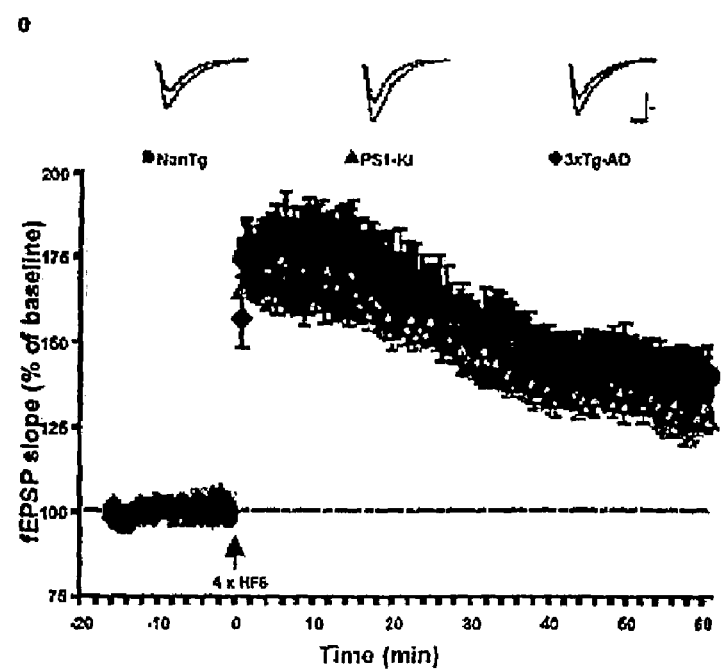
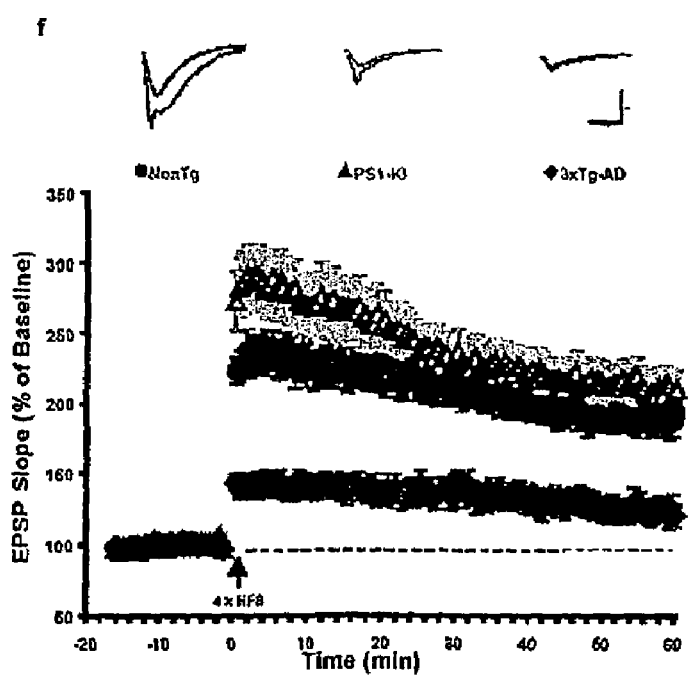
FIG. 14E-F

TRIPLE TRANSGENIC MOUSE MODEL OF ALZHEIMER'S DISEASE

CROSS-REFERENCE TO RELATED APPLICATION(S)

This application claims the benefit of U.S. Provisional Application Ser. No. 60/343,383, entitled "Triple Transgenic Mouse Model of Alzheimer's Disease," filed Dec. 20, 2001, the contents of which are hereby incorporated by reference in its entirety.

BACKGROUND OF THE INVENTION

The neuropathology of Alzheimer's Disease (AD) is characterized by two hallmark lesions: diffuse and neuritic plaques, which are predominantly composed of the amyloid-β (Aβ) peptide, and neurofibrillary tangles, which are composed of filamentous aggregates of hyperphosphorylated tau protein (Selkoe, D. J. (2001) Alzheimer's disease: genes, proteins, and therapy, *Phlysiol. Rev.* 81, 741-66). Loss of neuronal synaptic density and synapse number represent another invariant feature of the disease that appears to precede overt neuronal degeneration (DeKosky, S. T. & Scheff, S. W. (1990) Synapse loss in frontal cortex biopsies in Alzheimer's disease: correlation with cognitive severity. *Ann. Neurol.* 27,457-64; Scheff, S. W., Scott, S. A. & DeKosky, S. T. (1991) Quantitation of synaptic density in the septal nuclei of young and aged Fischer 344 rats. *Neurobiol. Aging* 12, 3-12).

Notably, the memory and cognitive decline observed in AD patients correlates better with the synaptic pathology than either plaques or tangles (Terry, R. D. et al. (1991) Physical basis of cognitive alterations in Alzheimer's disease: synapse loss is the major correlate of cognitive impairment, *Ann. Neurol.* 30, 572-80; Dickson, D. W. et al. (1995) Correlations of synaptic and pathological markers with cognition of the elderly, *Neurobiol. Aging* 16, 285-98; Sze, C. I. et al. (1997) Loss of the presynaptic vesicle protein synaptophysin in hippocampus correlates with cognitive decline in Alzheimer disease, *J. Neuropathol. Exp. Neurol.* 56, 933-44; Masliah, E. et al. (2001) Altered expression of synaptic proteins occurs early during progression of Alzheimer's disease, *Neurology* 56, 127-9), and is likely the most significant factor contributing to the initial stages of memory loss (Selkoe, D. J. (2002) Alzheimer's disease is a synaptic failure, *Science* 298, 789-91).

Gene-targeted and transgenic mice have proven to be invaluable for addressing some of the mechanisms underlying the synaptic dysfunction (Larson, J., et al. (1999) Alterations in synaptic transmission and long-term potentiation in hippocampal slices from young and aged PDAPP mice, *Brain Res.* 840, 23-35; Hsia, A. Y. et al. (1999) Plaque-independent disruption of neural circuits in Alzheimer's disease mouse models, *Proc. Natl. Acad. Sci. U.S.A.* 96, 3228-33; Chapman, P. F. et al. (1999) Impaired synaptic plasticity and learning in aged amyloid precursor protein transgenic mice, *Nat. Neurosci.* 2, 271-6; Fitzjohn, S. M. et al. (2001) Age-related impairment of synaptic transmission but normal long-term potentiation in transgenic mice that overexpress the human APP695SWE mutant form of amyloid precursor protein, *J. Neurosci.* 21, 4691-8), although none of these models recapitulate both hallmark pathological lesions (Wong, P. C., et al. (2002) Genetically engineered mouse models of neurodegenerative diseases, *Nat. Neurosci.* 5, 633-9). What is needed, therefore, is an animal model transgenic for multiple Alzheimer-related genes that produces multiple major features associated with this disease, including both hallmark pathological lesions.

In generating a transgenic animal such as a transgenic mouse, a human transgene is typically microinjected into fertilized eggs from a normal, nontransgenic mouse. Such transgenic mice have, in turn, been used to generate "double" transgenic mice by mating different strains of transgenic mice, each containing a different transgene, to produce a line containing both transgenes (i.e., a double transgenic mouse line)(See, e.g., U.S. Pat. No. 5,898,094). Similarly, a double transgenic mouse can be bred with a transgenic mouse containing a third transgene to generate a triple transgenic mouse.

The disadvantages of this process of breeding triple transgenic mice are several. First, it is exceedingly time consuming to produce a multiple transgenic mouse by a series of microinjection/breeding/screening/selection steps as described above. Second, this process is very costly as it requires extensive breeding, housing, screening, and personnel costs. Third, this process produces mice with a variable genetic background, which can be a major problem for therapeutic and behavioral investigations.

What is also needed, therefore, is a process for producing multiple transgenic mice that avoids one or more of the above-listed disadvantages.

SUMMARY OF THE INVENTION

One aspect of the invention is directed to a triple transgenic animal model for Alzheimer's disease.

Another aspect of the invention is directed to methods for generating multi-transgenic animals.

Another aspect of the invention is directed to methods for screening biologically active agents potentially useful for treating and/or ameliorating Alzheimer's disease (AD) or AD-type pathologies.

Another aspect of the invention is directed to compositions useful for treating AD or AD-type pathologies.

Another aspect of the invention is directed to methods of treating AD patients.

BRIEF DESCRIPTION OF THE DRAWINGS

FIG. 2 is a chart with data showing the success of the novel strategy for producing triple transgenic mice.

FIG. 7A is a Southern Blot showing DNA levels in selected candidate homozygous mice. FIG. 7B is a chart containing data showing successful breeding to homozygosity.

FIG. 9 is a photograph of sections of brains from a triple transgenic mouse (B1) and a control mouse (PS1-KI), stained with hematoxylin and eosin. CA3 is a region of the hippocampus, while DG is the Dentate Gyrus, another region of the brain. The arrows point to a pathological alteration, a tangle-like pathology, found in the brain sections taken from triple transgenic mice.

FIG. 14. Age related synaptic dysfunction in 3×Tg-AD mice. (A) Input/output (I/O) curves and representative fEPSPs at increasing stimulus strengths are shown for NonTg, $PS1_{M46V}$ KI, and 3×Tg-AD mice, showing no differences at one month of age. NonTg, 1.42±0.17 mV/ms, n=12 slices from 6 mice; PS1 KI, 0.60±0.06 mV/ms, in n=14/8, P<0.001; 3×Tg-AD, 0.53±0.06 mV/ms, n=14/6, P<0.001. (B) Smaller fEPSPs are evoked in six month $PS1_{M146V}$ KI and 3×Tg-AD mice as compared with NonTg mice, indicating impaired synaptic transmission. (C) Paired-pulse facilitation (PPF) was measured at an interpulse interval of 50 ms and was normal for all groups at one month of age. (D) At six months of age 3×Tg-AD mice exhibited normal PPF compared to NonTg mice but $PS1_{M146V}$ KI mice exhibited significantly enhanced PPF. (E) fEPSP slopes were recorded and were expressed as the percentage of the pre-tetanus baseline. Representative fEPSPs before (solid line) and 60 minutes after the induction of LTP (dotted line) are shown. LTP was normal in all groups at one month of age. (F) LTP was markedly impaired in 3×Tg-AD mice. In contrast, short-term LTP was enhanced in $PS1_{M146V}$ KI mice, but was otherwise normal. The amount of potentiation of fFPSPs between 0-10 minutes after HFS was 232±13% in NonTg mice (n=12 slices, 6 animals) and was significantly higher in $PS1_{M146V}$ KI mice (282±19%, n=14 slices, 8 animals, P<0.05) but was significantly reduced in 3×Tg-AD mice (143±6%, n=14 slices, 6 animals, P<0.001). The amount of potentiation between 50-60 minutes after HFS was 190±11% in NonTg mice and was not significantly different in $PS1_{M146V}$ KI Mice (212±13%, P<0.1), but was significantly reduced in 3×Tg-AD mice (125±8%, P<0.001).

DETAILED DESCRIPTION OF THE INVENTION

Figure 1:
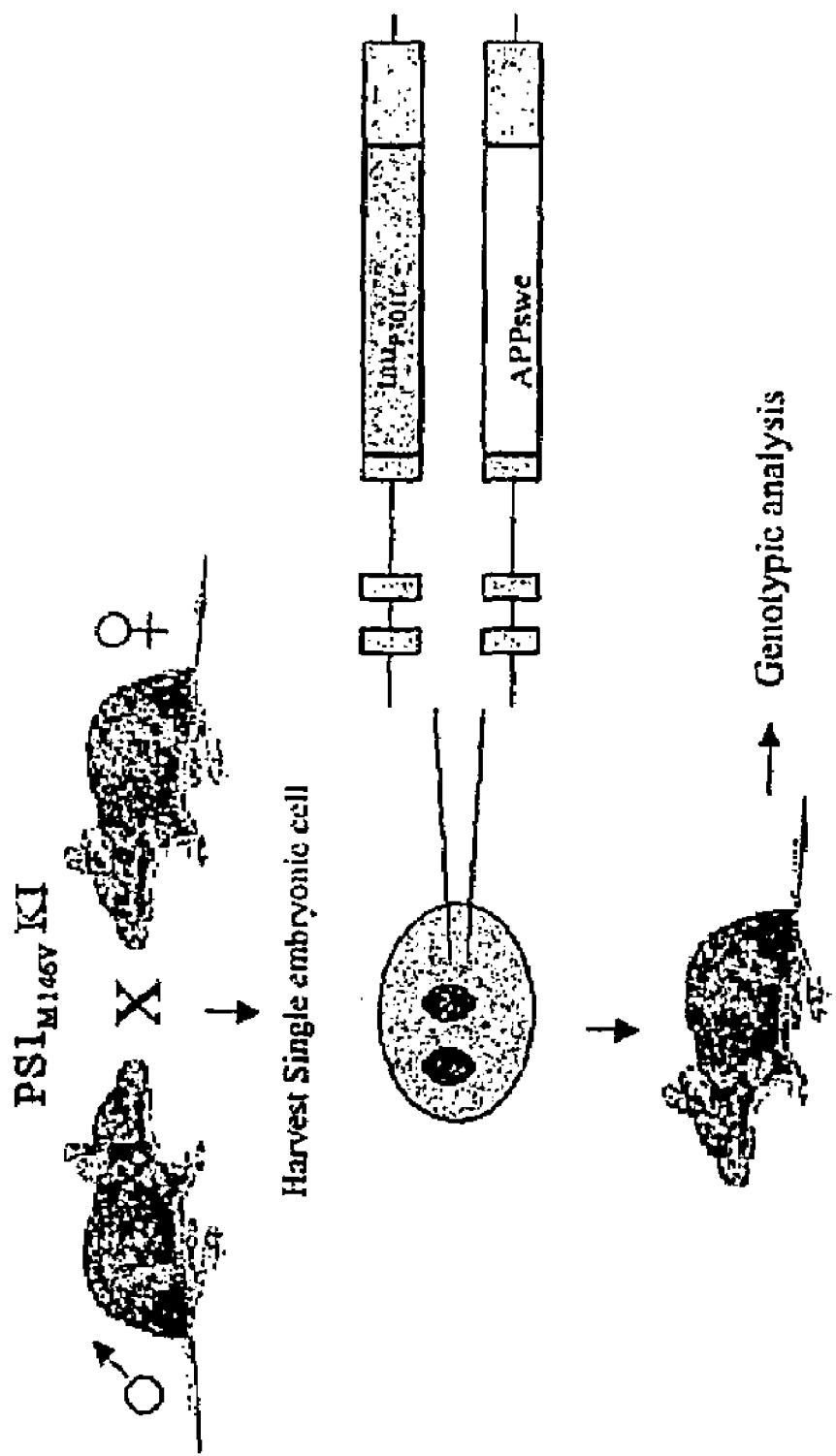
FIG. 1 is a diagram illustrating the design of a novel strategy for the generation of the 3×Tg-AD mouse model. Single cell embryos were harvested from mutant homozygous $PS1_{M146V}$ knockin mice. Using the pronuclear microinjection technique, two independent transgenic constructs encoding human $APP_{Swe}$ and $tau_{P301L}$ (4R/0N), under the control of the mouse Thy1.2 regulatory elements, were co-injected. The entire mouse Thy1.2 genomic sequence is shown with exons depicted as boxes and noncoding sequences as thin lines. The injected embryos were re-implanted into foster mothers and the resulting offspring genotyped to identify 3×Tg-AD mice.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The term "transgene" refers to the genetic material which has been or is about to be artificially inserted into the genome of an animal, particularly a mammal and more particularly a mammalian cell of a living animal.

"Transgenic animal" refers to a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

"Operably linked" means that a DNA sequence and a regulatory sequence(s) are connected in such a way as to permit gene expression when the appropriate transcriptional activator proteins are bound to the regulatory sequence(s). For example, a nucleic acid sequence encoding human amyloid-β precursor protein (βAPP) may be operably linked to a mouse Thy1.2 promoter to facilitate production of βAPP polypeptide in mouse cells.

"Aβ pathology" refers to diffuse and neuritic plaques observed in the brain, which are predominantly composed of the amyloid-β(Aβ) peptide. Aβ pathology also includes neuronal and/or glial inclusions or insoluble deposits that stain positively with anti-Aβ antibodies.

"Tau pathology" refers to neurofibrillary tangles observed in the brain, including one or more of paired helical filaments (PHFs), straight Tau filaments, and any other type of Tau filament. Tau pathology also includes neuronal and/or glial inclusions or insoluble deposits that stain positively with anti-Tau antibodies.

"AD pathology" refers to pathological changes in AD patients, for example, Aβ pathology, Tau pathology, loss of neuronal synaptic density and synapse number, decreased cognitive ability, memory loss and other pathologies associated with AD.

"AD-associated polypeptides" refers to polypeptides, wild-type or mutant, known to be associated with AD and AD-related pathologies, such as Aβ pathology and Tau pathology. AD-associated polypeptides include, but are not limited to, Presenilin, βAPP, and Tau.

"Heterologous polypeptides" refers to the polypeptides, wild-type or mutant, expressed by transgenes in a transgenic animal. Examples of heterologous polypeptides may include human Presenilin, Tau, βAPP and other AD-associated polypeptides expressed in a non-human animal.

Introduction

One aspect of the instant invention is directed to a triple transgenic animal model of Alzheimer's disease. In one example, two human genes were inserted into the genome of a genetically-altered mouse already containing a human gene, thereby producing a triple transgenic mouse.

Another aspect of the instant invention is directed to a process for producing a multi-transgenic animal in general. Typically, transgenic mice are generated by microinjecting a foreign gene into fertilized eggs isolated from a normal, non-transgenic, mouse. In the instant invention, it has been shown that it is possible to create a mouse expressing additional human transgenes by starting with a mouse that is already transgenic. That is, single-cell embryos (fertilized eggs) from an existing transgenic mouse have been harvested and additional transgene DNA fragments have been microinjected into the cells. The results shown herein demonstrate that existing fertilized eggs from transgenic mice can withstand the microinjection process and that it is possible to simultaneously co-microinject more than one type of transgene DNA fragment to successfully produce a multi-transgenic mouse.

The advantage to this process is that it permits the production of a multi-transgenic mouse on the same genetic background. In addition, it is possible to readily and easily breed multi-transgenic mice. Previously, the generation of a multi-transgenic mouse required extensive breeding strategies and led to the production of mice with a mixed genetic background, a confounding variable in research aimed at behavioral, pharmacological and therapeutic studies.

Although the process for generating a multi-transgenic animal is described herein with reference to a multi-transgenic mouse model for Alzheimer's disease, one of skill in the art will appreciate that the described process may be used to generate multi-transgenic animals other than mice, for example, rats, hamsters, rabbits, etc., using transgenes other than those related to AD and AD-type pathologies. The present invention of a method for generating multi-transgenic animals is not intended to be limited to the particular triple transgenic mouse model of AD described below but rather may be applied to any non-human animal model in which it is desirable to express multiple transgenes.

The novel triple transgenic mouse model produced in the instant invention contains the three major genes that contribute to the hallmark pathological features of Alzheimer's disease. Starting with a transgenic mouse obtained from Dr. Mark Mattson of the NIH, this transgenic mouse model was improved by the introduction of two additional transgenes that encode human genes that contribute to Alzheimer's disease pathology, using a novel strategy that did not require crossing mouse lines. These mice are exceedingly valuable for therapeutic investigations and for basic research aimed at understanding the behavioral, physiological, molecular/cell biological and pharmacological processes leading to dementia in an animal model.

This novel triple transgenic model (3×Tg-AD) that is the first transgenic model to develop both Aβ and Tau pathology in AD-relevant brain regions. 3×Tg-AD mice develop extracellular Aβ deposits prior to tangle formation, consistent with the amyloid cascade hypothesis. These mice exhibit deficits in synaptic plasticity, including long-term potentiation (LTP) that occurs prior to extracellular Aβ deposition and tau pathology, but associated with intracellular Aβ immunoreactivity. Such findings suggest that synaptic dysfunction is a proximal defect in the pathobiology of Alzheimer's disease that precedes the development of extracellular plaque formation and tau pathology. These 3×Tg-AD mice may now be used to assess the efficacy of anti-Aβ therapies in mitigating synaptic dysfunction and tau-mediated neurodegeneration.

Transgenic Animals

Transgenic animals comprise exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACs, and the like. Generally, transgenic animals are mammals, most typically mice.

The exogenous nucleic acid sequence may be present as an extrachromosomal element or stably integrated in all or a portion of the animal's cells, especially in germ cells. Unless otherwise indicated, a transgenic animal comprises stable changes to the germline sequence. During the initial construction of the animal, chimeric animals (chimeras) are generated, in which only a subset of cells have the altered genome. Chimeras may then be bred to generate offspring heterozygous for the transgene. Male and female heterozygotes are may then be bred to generate homozygous transgenic animals.

Typically, transgenic animals are generated using transgenes from a different species or transgenes with an altered nucleic acid sequence. For example, a human gene, such as the nucleic acid encoding βAPP or Tau, may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions. For example, an introduced human βAPP gene may be wild type or may include a mutation such as the previously-characterized "Swedish mutation." Where the introduced gene is a coding sequence, it is usually operably linked to a promoter, which may be constitutive or inducible, and other regulatory sequences required for expression in the host animal.

Nucleic Acid Compositions

Constructs for use in the present invention include any construct suitable for use in the generation of transgenic animals having the desired levels of expression of a desired transgene as, for example, Presenilin-, Tau-, or βAPP-encoding sequence, other AD-associated polypeptide-encoding sequence, or other heterologous polypeptide-encoding sequence. Methods for isolating and cloning a desired sequence, as well as suitable constructs for expression of a selected sequence in a host animal, are well known in the art. In addition to the heterologous polypeptide-encoding sequences, the construct may contain other sequences, such as a detectable marker.

The heterologous polypeptide-encoding construct can contain a wild-type sequence or mutant forms, including nucleotide insertions, deletions, splice variants, and base substitutions. An AD-associated polypeptide-encoding construct having nucleotide insertions, deletions, splice variants, or base substitutions associated with AD and/or AD-type pathologies in humans is one example of a useful construct.

The heterologous polypeptide-encoding construct may include the open reading frame encoding specific polypeptides, introns, and adjacent 5' and 3' non-coding nucleotide sequences involved in the regulation of expression. The heterologous polypeptide-encoding portion of the construct may be cDNA or genomic DNA or a fragment thereof The genes may be introduced into an appropriate vector for extrachromosomal maintenance or for integration into the host.

The nucleic acid compositions used in the subject invention may encode all or a part of the heterologous polypeptide-encoding sequence as appropriate. Fragments may be obtained of the DNA sequence by chemically synthesizing oligonucleotides in accordance with conventional methods, by restriction enzyme digestion, by PCR amplification, and by other techniques known in the art.

The Presenilin-1 Mutant Knock-in Mouse

Mutations in the presenilin-1 (PS1) gene on chromosome 14 have been causally linked to many cases of early-onset inherited AD. PS1 mutant "knock-in" mice ($PS1_{M146V}$), in which a homologous exon in the mouse PS1 gene has been replaced with an AD-linked PS1 mutation, have been previously described (Guo, Q. et al. (1999) Increased vulnerability of hippocampal neurons to excitotoxic necrosis in presenilin-1 mutant knock-in mice, *Nat. Med.* 5, 101-6). In the homozygous state, such mice produce only mutant PS1 and no wild-type PS1. Moreover, the mutant PS1 has been "humanized" in these mice by the introduction of a second mutation, an I145V substitution.

The APP Gene and its Derivatives Suitable for Use in the Present Invention

The APP gene has been described in U.S. Pat. No. 6,455,757, the entire contents of which are hereby incorporated by reference.

Transgenic animals of the present invention comprise a heterologous sequence encoding a desired APP gene, preferably a human βAPP gene. Preferably, the host animal produces high levels of human βAPP or its proteolytic fragments, such as human $Aβ_{42}$. Preferably, the βAPP gene encodes a genomic βAPP sequence or a sequence encoding a spliced βAPP gene (e.g., a cDNA), more preferably a full-length human βAPP cDNA sequence. Alternatively, the βAPP gene can be a mutant, particularly an βAPP mutant associated with AD and/or an AD-type pathology. Mutants of particular interest include human βAPP cDNA harboring the Swedish double mutation.

Several isoforms and homologs of βAPP are known. Additional homologs of cloned βAPP are identified by various methods known in the art. For example, nucleic acids having sequence similarity are detected by hybridization under low stringency conditions. Labeled nucleotide fragments can be used to identify homologous βAPP sequences as, for example, from other species.

The host animals can be homozygous, hemizygous or heterozygous for the βAPP-encoding sequence, preferably homozygous. The βAPP gene can also be operably linked to a promoter to provide for a desired level of expression in the host animal and/or for tissue-specific expression. Expression of βAPP can be either constitutive or inducible.

βAPP genes suitable for use in the present invention have been isolated and sequenced. The sequence for human β-amyloid precursor protein is found at GenBank Accession No. XM047793. See also, Table 2 of U.S. Pat. No. 6,455,757, providing a list of human APP sequences with Genbank accession numbers relating to the listed APP sequences.

The Tau Gene and its Derivatives Suitable for use in the Present Invention

The tau gene encodes the microtubule associated protein Tau that is the major component of the PHFs that make up the characteristic tangles seen in AD and other neurodegenerative disorders. The human Tau protein found in brain is encoded by eleven exons. The sequence of the wild-type human tau gene is described by Andreadis, A. et al. (1992) *Biochemistry*, 31:10626-10633. The sequence for the human tau gene is found at GenBank Accession No. 11426018.

Transgenic animals of the present invention comprise a heterologous sequence encoding a desired tau gene, preferably a human tau gene. Preferably, the host animal produces high levels of human tau or its proteolytic fragments. Preferably, the tau gene encodes a genomic tau sequence or a sequence encoding a spliced tau gene (e.g., a cDNA), more preferably a full-length human tau cDNA sequence. Alternatively, the tau gene can be a mutant, particularly a tau mutant associated with AD and/or an AD-type pathology. Mutants of particular interest include human tau cDNA harboring the P301L mutation. Other mutants of the tau gene suitable for use in the present invention are described in U.S. Pat. No. 6,475,723, the entire contents of which are hereby incorporated by reference.

Several isoforms and homologs of tau are known. Additional homologs of cloned tau are identified by various methods known in the art. For example, nucleic acids having sequence similarity are detected by hybridization under low stringency conditions. Labeled nucleotide fragments can be used to identify homologous tau sequences as, for example, from other species.

The host animals can be homozygous, hemizygous or heterozygous for the Tau-encoding sequence, preferably homozygous. The tau gene can also be operably linked to a promoter to provide for a desired level of expression in the host animal and/or for tissue-specific expression. Expression of tau can be either constitutive or inducible.

Methods of Making Transgenic Animals

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Specific methods of preparing the transgenic animals of the invention as described herein. However, numerous methods for preparing transgenic animals are now known and others will likely be developed. See, e.g., U.S. Pat. Nos. 6,252,131, 6,455,757, 6,028,245, and 5,766,879, all incorporated herein by reference. Any method that produces a transgenic animal expressing multiple AD-associated polypeptides is suitable for use in the practice of the present invention. The microinjection technique described is particularly useful for incorporating transgenes into the genome without the accompanying removal of other genes.

Drug Screening Assays

The transgenic animals described herein may be used to identify compounds useful in the treatment of AD and/or AD-related pathologies. For example, transgenic animals of the present invention may be treated with various candidate compounds and the resulting effect, if any, on the formation of diffuse and neuritic plaques and neurofibrillary tangles, and/or the on the loss of neuronal synaptic density and synapse number evaluated. The effect of candidate compounds on cognition and memory may also be evaluated in transgenic animals of the present invention, using techniques known in the art. Preferably, the compounds screened are suitable for use in humans.

Drug screening assays in general suitable for use with transgenic animals are known. See, for example, U.S. Pat. Nos. 6,028,245 and 6,455,757. Immunoblot analyses, expression studies, measurement of Aβ proteolytic fragments by ELISA, immunocytochemical and histological analysis of brain sections suitable for use with the transgenic animal of the present invention are described herein. However, it will be understood by one of skill in the art that many other assays may also be used. The subject animals may be used by themselves, or in combination with control animals. Control animals may have, for example, wild-type βAPP, tau, and/or presenilin transgenes that are not associated with AD, or may be transgenic for a control construct that does not contain a Presenilin, Tau or βAPP-encoding sequence. The screen using the transgenic animals of the invention can employ any phenomena associated with AD or AD-related pathologies that can be readily assessed in an animal model.

Therapeutic Agents

Once compounds have been identified in drug screening assays as eliminating or ameliorating the effects of AD and/or AD-related pathologies, these compounds can be used as therapeutic agents, provided they are biocompatible with the animals, preferably humans, to whom they are administered.

The therapeutic agents of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. Administration of the compounds can be administered in a variety of ways known in the art, as, for example, by oral, buccal, rectal, parenteral, intraperitoneal, intradermal, transdermal, intratracheal, etc., administration.

Depending upon the particular route of administration, a variety of pharmaceutically acceptable carriers, well known in the art can be used. These carriers include, but are not limited to, sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water. Preservatives and other additives can also be present. For example, antimicrobial, antioxidant, chelating agents, and inert gases can be added (see, generally, Remington's Pharmaceutical Sciences, 16th Edition, Mack, (1980)).

The concentration of therapeutically active compound in the formulation may vary from about 0.1-100 wt. %.

Those of skill will readily appreciate that dose levels can vary as a function of the specific therapeutic agents, the severity of the symptoms and the susceptibility of the subject to side effects. Preferred dosages for a given therapeutic agent are readily determinable by those of skill in the art by a variety of means. A preferred means is to measure the physiological potency of a given therapeutic agent.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used(e.g., amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Materials and Methods

ELISAs and Immunoblots. Aβ ELISAs were performed essentially as described previously (Suzuki, N. et al. (1994) An increased percentage of long amyloid beta protein secreted by familial amyloid beta protein precursor (beta APP717) mutants, *Science* 264, 1336-40). For immunoblots, brains extracted from transgenic and control mice were dounce homogenized in a solution of 2% SDS in $H_2O$ containing 0.7 mg/ml Pepstatin A supplemented with complete Mini protease inhibitor tablet (Roche, No. 1836153). The homogenized mixes were briefly sonicated to sheer the DNA and centrifuged at 4° C. for 1 hour at 100,000 g. The supernatant was used for immunoblot analysis. Proteins were resolved by SDS/PAGE (10% Bis-Tris from Invitrogen) under reducing conditions and transferred to nitrocellulose membrane. The membrane was incubated in a 5% solution of not-fat milk for 1 hour at 20° C. After overnight incubation at 4° C. with primary antibody, the blots were washed in tween-TBS for 20 minutes and incubated at 20° C. with secondary antibody. The blots were washed in T-TBS for 20 minutes and incubated for 5 minutes with Super Signal (Pierce).

Immunohistochemistry. Formalin-fixed, paraffin-embedded brains were sectioned at 5 μm and mounted onto silane-coated slides and processed as described. The following antibodies were used: anti-Aβ 6E10 and 4G8 (Signet Laboratories, Dedham, Mass.), anti-Aβ 1560 (Chemicon), anti-APP 22C11 (Chemicon), anti-Tau HT7, AT8, AT180 (Innogenetics), Tau C17 (Santa Cruz), Tau 5 (Calbiochem), anti-GFAP (Dako), and anti-actin (Sigma). Primary antibodies were applied at dilutions of 1:3000 for GFAP, 1:1000 for 6E10, 1:500 for 1560, AT8, AT180 and Tau5, and 1:200 for HT7.

Electrophysiology. Mice were anaesthetized with halothane, decapitated and the brains were rapidly removed in ice-cold artificial cerebrospinal fluid (aCSF; 125 mM NaCl, 2.5 MM KCl, 1.25 mM KH2PO4, 25 mM NaHCO3, 1.2 mM MgSO4, 2 mM CaCl2, and 10 mM dextrose, bubbled with 95% $O_2$-5% $CO_2$, pH 7.4). Transverse hippocampal slices (400 μm) were prepared in aCSF using a vibroslice, and left to equilibrate for at least 1 hour prior to recording in a holding chamber containing aCSF at room temperature.

Slices were placed in an interface chamber, continuously perfused with aCSF at 34° C. and covered with a continuous flow of warmed humidified gas (95% $O_2$, 5% $CO_2$). Field excitatory post-synaptic potentials (fEPSPs) were recorded in the stratum radiatum of the CA1 using glass microelectrodes (1-5Ω,~5 μm diameter) filled with aCSF. Synaptic responses were evoked by stimulation of the Schaffer collateral/commissural pathway with a concentric bipolar stimulating electrode with 0.1 ms pulse-width. Input/output curves were generated using stimulus intensities from 0 to 300 μA in increments of 20 μA. PPF was assessed using an interstimulus interval of 50 ms. Baseline fEPSPs were evoked at ~30% of the max fEPSP for 15 minutes prior to high frequency stimulation (HFS). LTP was induced at baseline intensity using HFS consisting of 4 trains of 100 Hz stimulation at 20 s intervals. Recordings were made every 30 s for 60 minutes after HFS. The maximum fEPSP slopes were measured offline using Axograph software, and were expressed as a percentage of the average slope from the 15 minutes of baseline recordings. In some experiments the stimulus intensity was raised so that baseline EPSP slopes matched the average baseline EPSP in the NonTg mice (usually an EPSP ~0.7 mV in amplitude). Data were expressed as mean±S.E.M, and assessed for significance using the Student's t test.

Example 2

$F_1$ Hemizygous Triple Transgenic Mice

Generation of $F_1$ Transgenic Mice. Presenilin-1 knockin ($PS1_{M146V}$KI) mice were provided by Dr. Mark Mattson of the National Institutes of Health (NIH). The derivation and characterization of the $PS1_{M146V}$KI mice are described in Guo et al. (1999) *Nat. Med.* 5: 101-106; see also, Leissring, et al. (2000) *J. Cell Biol.* 149: 793-797.

The triple transgenic mice were created by first harvesting single cell embryos from homozygous mutant presenilin-1 knockin mice (harboring the M146V mutation). Two transgenes were simultaneously microinjected into these single cell embryos using the pronuclear microinjection technique.

The two transgenes contained cDNA molecules encoding either the human Swedish APP mutation or the P301L mutation in the human tau gene. Both of these cDNA molecules were separately inserted into the mouse Thy1.2 gene cassette, allowing expression to be under the regulatory control of this sequence. The microinjected embryos were then transferred to foster mother mice and three weeks later pups were born.

These pups were screened to identify which ones contained the transgenes by Southern blot analysis. Five of the lines were found to contain both transgenes and were backcrossed to homozygous mutant presenilin-1 knockin mice. By backcrossing the mice to homozygous mutant presenilin-1 knockin mice, the mutant presenilin-1 transgene has been maintained on a homozygous background and the mutant tau and APP transgenes on a hemizgygous background. The mice were subsequently bred such that all three transgenes (presenilin-1, APP, and tau) are on a homozygosity, as discussed below.

The novel strategy used to generate the multi-transgenic mouse is shown in FIG. 1. Two mice transgenic for the mutant human gene presenilin-1 knockin ($PS1_{M146V}$)were mated and the resulting fertilized eggs (embryonic cells) harvested. A single embryonic cell was co-microinjected with Thy1.2-$APP_{SW695}$ and Thy1.2-$TAU_{P301L}$, then implanted into a foster mother. The resulting offspring were founders of a multi-transgenic (in this case, a $PS1_{M146V}$KI/$APP_{SW695}$/$TAU_{P301L}$ triple-transgenic or "3xTg-AD") mouse line.

As will be appreciated, this process is a much simpler, faster and cost-effective method for producing a multi-transgenic mouse than previous breeding strategies, as the breeding and genotyping of the mouse colony is greatly reduced.

Plasmids containing the tau(P301L) gene and the APPswe gene were provided by Dr. Michael Hutton and Dr. Rachel Neve, respectively. The sequence for human β-amyloid precursor protein is found at GenBank Accession No. XM047793. The sequence for human tau gene is found at GenBank Accession No. 11426018.

The Thy1.2 gene was a gift from Dr. Pico Caroni. The sequence for the Thy 1.2 gene is found at GenBank Accession No. M12379.

Founder Lines. FIG. 2 shows a chart containing the relevant genotype for six founder lines resulting from the co-microinjection strategy described above and shown in FIG. 1. As indicated in FIG. 2, all of the founder lines are homozygous for $PS1_{M146V}$KI, and five of the six lines, designated A2, B1, F5, F7, and G6, are hemizygous for both $APP_{SWE}$ and $Tau_{P301L}$. One of the founder lines, designated A1, is hemizygous only for $Tau_{P301L}$.

Expression Studies. Immunoblots containing protein (80 μg) from three founder lines and one non-transgenic control were probed with TauC17, an antibody that detects both mouse and human Tau protein, and HT7, an antibody specific for human Tau protein. TauC17 antibody was from Santa Cruz, Cat. No. SC-1995. The HT7 antibody was from Innogenetics, Cat. No. BR-01.

Figure 3:
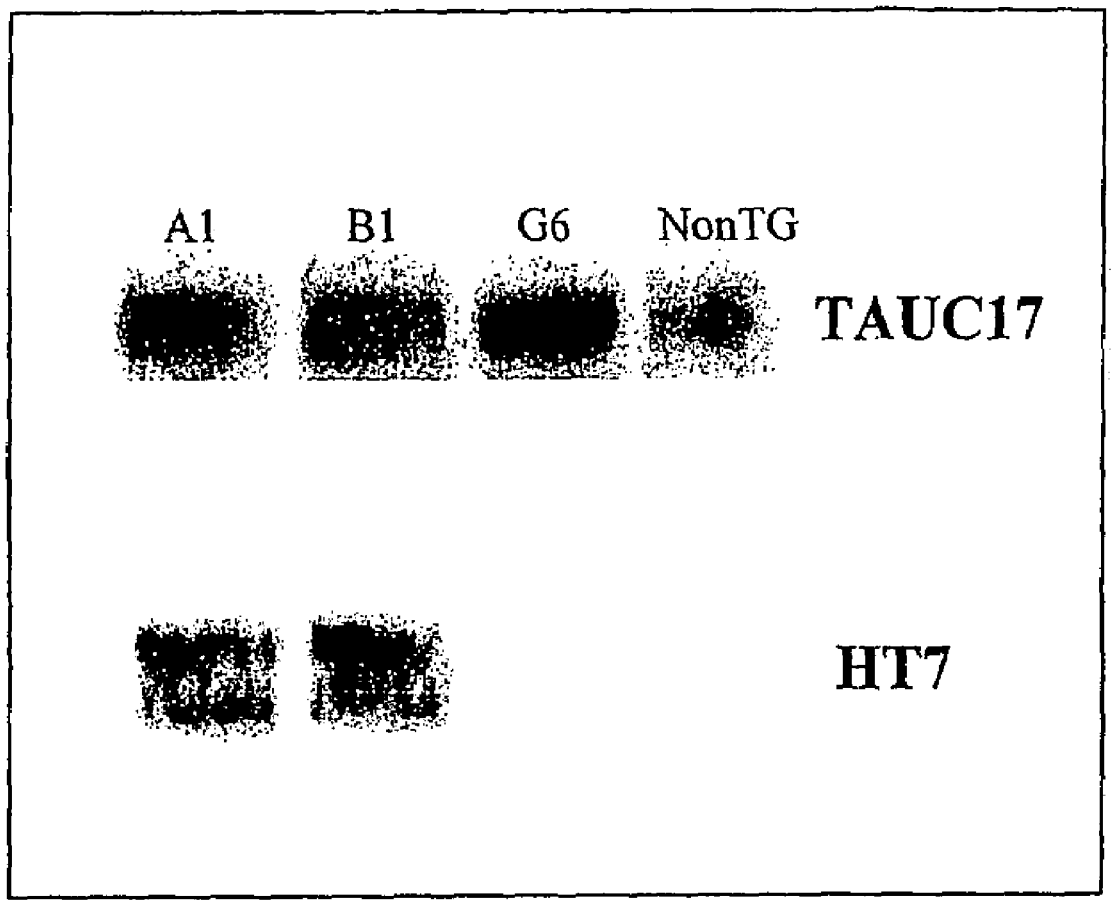
FIG. 3 is an autoradiogram of a Western Blot demonstrating expression of human tau protein in triple transgenic mice. TAUC17 is an antibody that detects both human and mouse Tau protein. HT7 is an antibody that is specific for human Tau protein.

The results are shown in FIG. 3. As shown, two of the founder mouse lines, A1 and B1, expressed human Tau protein (the double bands are due to isoforms of the Tau protein). The G6 line also expresses low levels of the human Tau protein, detected with this human specific protein, but high levels of the mouse tau protein (data not shown).

Figure 4:
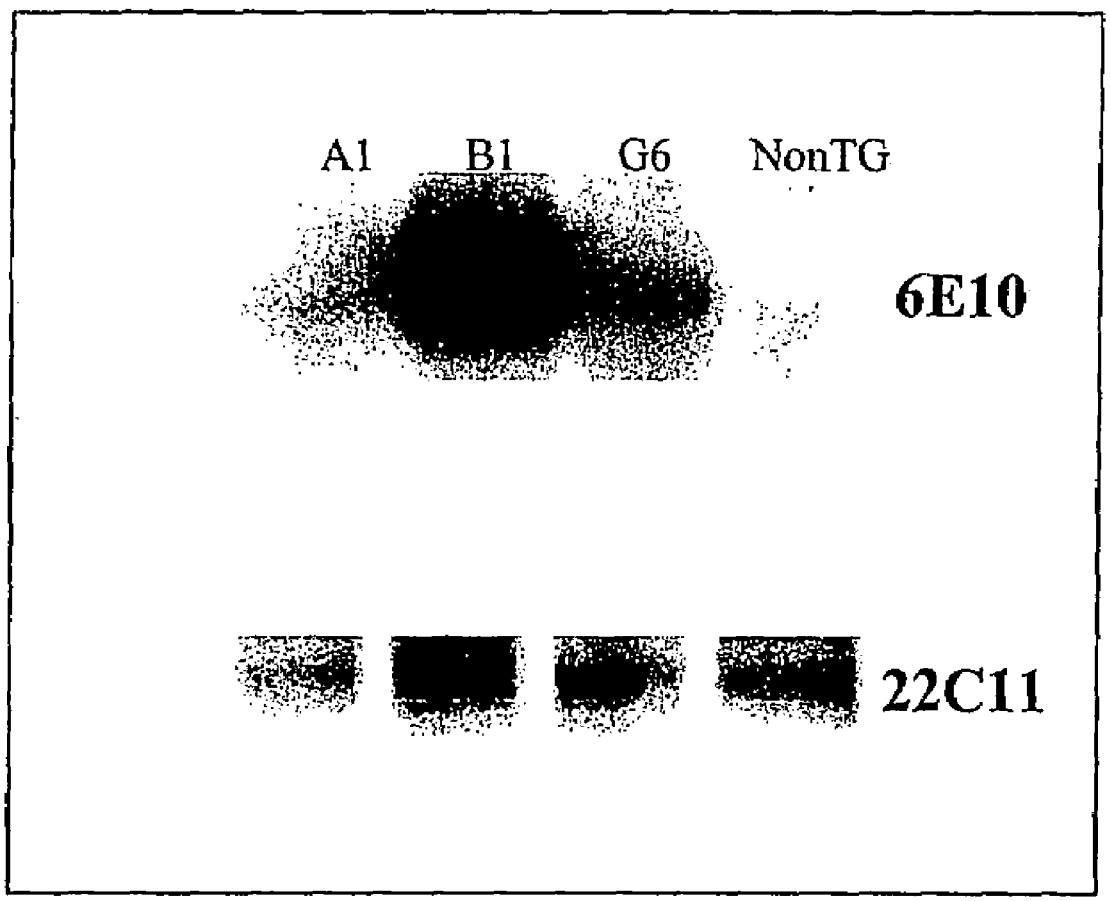
FIG. 4 is an autoradiogram of a Western Blot demonstrating expression of human APP protein in triple transgenic mice. 22C11 is an antibody that detects both human and mouse APP protein. 6E10 is an antibody that is specific for human APP protein.
Figure 5:
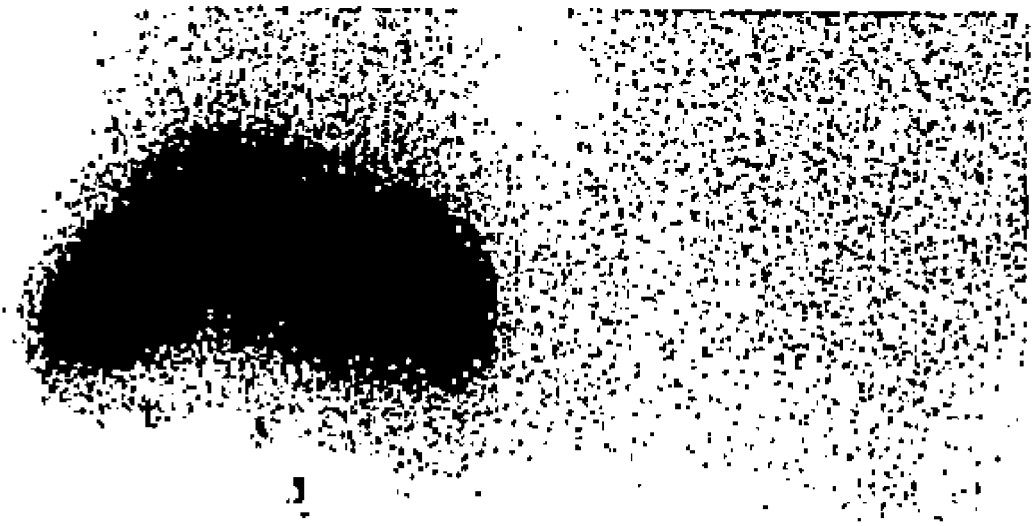
FIG. 5 is an autoradiogram of a Western blot demonstrating expression of C99 protein in brain tissue of triple transgenic mice.

Similarly, as shown in FIG. 4, immunoblots containing protein from three founder lines and one non-transgenic control were probed with 22C11, an antibody that detects both mouse and human APP protein, and 6E10, an antibody specific for human APP protein. The 22C11 antibody was from Chemicon International, Cat. No. MAB348. The 6E10 antibody is from Signet, Cat. No. 9320-02. As is apparent, founder mouse line B1, shown to express human Tau protein in FIG. 3, also expressed human APP protein. When full length APP protein is treated with β-secretase, a proteolytic fragment, C99, is produced that is the immediate precursor for the highly amyloidogenic amyloid-62 (Aβ) peptide. In FIG. 5, protein isolated from the brain of a B1 triple-transgenic 3×Tg-AD mouse and from the brain of a presenilin-1 knockin control mouse was probed with 6E10. The C99 fragment was found only in tissue from the B1 triple transgenic mouse, indicating that the B1 mouse both expressed and processed APP protein from the human transgene.

Figure 6:
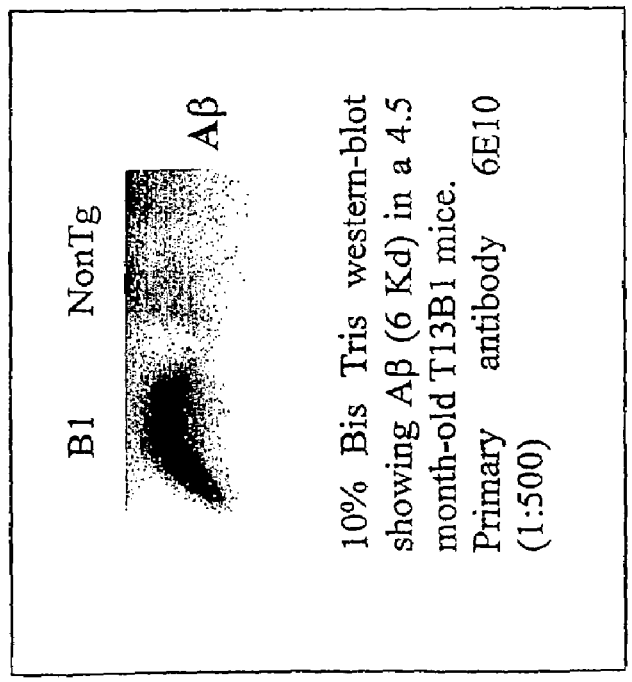
FIG. 6A is an autoradiogram of a Western blot demonstrating expression of Aβ protein in a triple transgenic mouse.
FIG. 6B is a chart showing ELISA results further demonstrating Aβ expression in triple transgenic mice.

This is further demonstrated in FIG. 6, wherein it is shown that a B1 mouse (T13B1) also processed APP to Aβ. In FIG. 6A, a Western blot containing protein from T13B1 mice and from nontransgenic control mice were probed with a 1:500 dilution of primary antibody 6E10. The B1 mouse, but not the control mouse, expressed the Aβ fragment of APP.

ELISA tests were used to measure the two isoforms of Aβ, namely, Aβ 40 and Aβ 42, in B1 mice and in transgenic control mice Tg2576, known to express high levels of Aβ. The Aβ 42 isoform is the more amyloidogenic of the two isoforms, and the ratio of Aβ 42 to Aβ 40 (42/40) is increased in Alzheimer patients.

As shown in FIG. 6B, B1 mice express both Aβ isoforms, but have a higher 42/40 ratio than the Tg2576 control mice, suggesting that the B1 triple transgenic nice more closely exhibit traits consistent with Alzheimer's disease and, accordingly, provide an improved mouse model of this disease.

As discussed above, $F_1$ hemizygous triple transgenic mice were generated by co-microinjecting two independent transgenes encoding human $APP_{Swe}$ and human $tau_{P301L}$, both under control of the mouse Thy1.2 regulatory element, into single-cell embryos harvested from homozygous mutant $PS1_{M146V}$ knockin (KI) mice (FIG. 1). Genotype analysis by Southern blotting indicated that the tau and APP transgenes co-integrated at the same locus, a finding further corroborated by analysis of the transmission frequency in subsequent generations (data not shown).

Because the APP and tau transgenes are unlikely to independently assort and because the M146V mutation was "knocked in" to the endogenous mouse PS1 locus 15, these 3×Tg-AD mice essentially breed as readily as a "single" transgenic line, even though the mice contain three transgenes. This facilitates the establishment and maintenance of the mouse colony and reduces the need for genotypic analysis of the progeny. Moreover, this strategy results in another important pragmatic benefit as the 3×Tg-AD mice are of the same genetic background, thereby eliminating a confounding biological variable that is unavoidable when crossing independent transgenic lines.

Example 3

Homozygous Triple Transgenic Mice

In order to generate mice homozygous for all three transgenes ($PS1_{M146V}$, $tau_{P301L}$, $APP_{Swe}$), hemizygous F1 mice were crossed to each other. FIG. 7 shows a southern blot identifying potential candidate homozygous mice. Homozygous mice have double the gene dosage compared to hemizygous mice, as may be visualized by southern blotting. Such data may be confirmed by crossing the potential homozygous animal to a normal, nontransgenic mouse. If the mouse is homozygous, as predicted by the southern blot, all of the offspring will be positive for the transgenic trait. The results of such crosses are shown in the table in FIG. 7. As indicated by the Comments section of the table, in which the number of positive transgenic mice identified and the number of mice generated are shown, all of the candidate mice proved to be homozygous as 100% of their offspring were transgenic.

Figure 8:
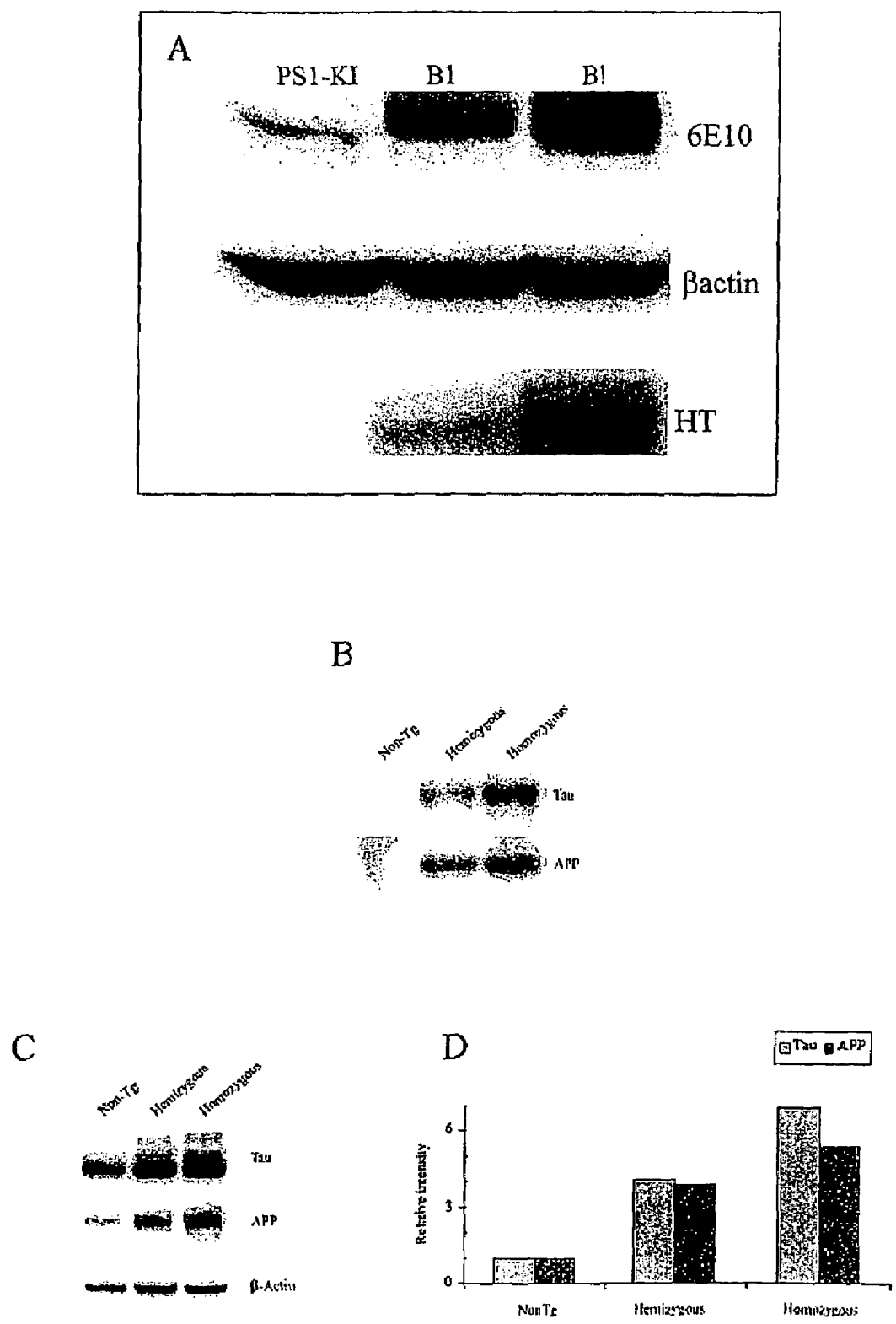
FIG. 8A is a Western blot showing that homozygous triple transgenic mice express both human TAU and human APP at twice the levels of hemizygous mice. β actin is shown as a control.
FIG. 8B is a representative Southern blot comparing the gene dosage of the tau and APP transgenes from tail DNA of hemizygous and homozygous mice.
FIG. 8C is an immunoblot comparing steady state levels of human APP and tau proteins in the brains of 4-month old hemizygous and homozygous 3×Tg-AD mice. For both APP (detected with antibody 22C11) and tau (detected with antibody tau5), the levels are doubled in the homozygous mice.
FIG. 8D is a bar graph showing steady state levels of the βAPP and tau protein are approximately 3-to-4-fold and 6-to-8 fold higher than endogenous levels in hemizygous and homozygous mice, respectively.

In FIG. 8A, protein from both hemizygous and homozygous B1 triple transgenic mice, as well as from control presenilin-1 knockin single transgenic mice, was probed with 6E10 antibody to human APP, HT7 antibody to human Tau protein, or an antibody to β-actin (a control used to ensure that equal amounts of protein from each mouse line were loaded onto the gel used to produce the immunoblot). As expected, both B1 mouse lines expressed both Tau and APP proteins, with the homozygous B1 mice expressing twice the amount of Tau and APP protein as the hemizygous B1 mice. The presenilin-1 knockin mice show no Tau protein and only a small amount of APP protein, resulting from cross-reactivity with mouse APP protein.

A doubling of gene dosage is also apparent in selected mice by Southern blotting (FIG. 8B). Besides further facilitating the breeding and maintenance of this mouse colony, the expression levels of human tau and APP transgene products are doubled in the homozygous mice (FIG. 8C). Steady-state levels of both tau and APP approach about 3-to 4-fold and about 6-to 8-fold endogenous levels in the brains of the hemizygous and homozygous mice, respectively (FIG. 8D). The maintenance of both hemizygous and homozygous 3×Tg-AD mice renders it possible to study the effect these gene interactions exert as a function of age in a context in which the expression levels are doubled in mice of the same genetic background.

Example 4

Pathological Alterations in the Triple Transgenic Mice

Sections from the brains of B1 triple transgenic mice and PS1-KI control (single transgenic) nice were prepared and stained with hematoxylin and eosin. The brain section from B1 mice (FIG. 9) exhibits a tangle-like pathology, indicated by the arrows, similar to that seen in the brains of Alzheimer patients. This pathological alteration is not seen in the brain sections taken from PS1-KI control mice.

Figure 10:
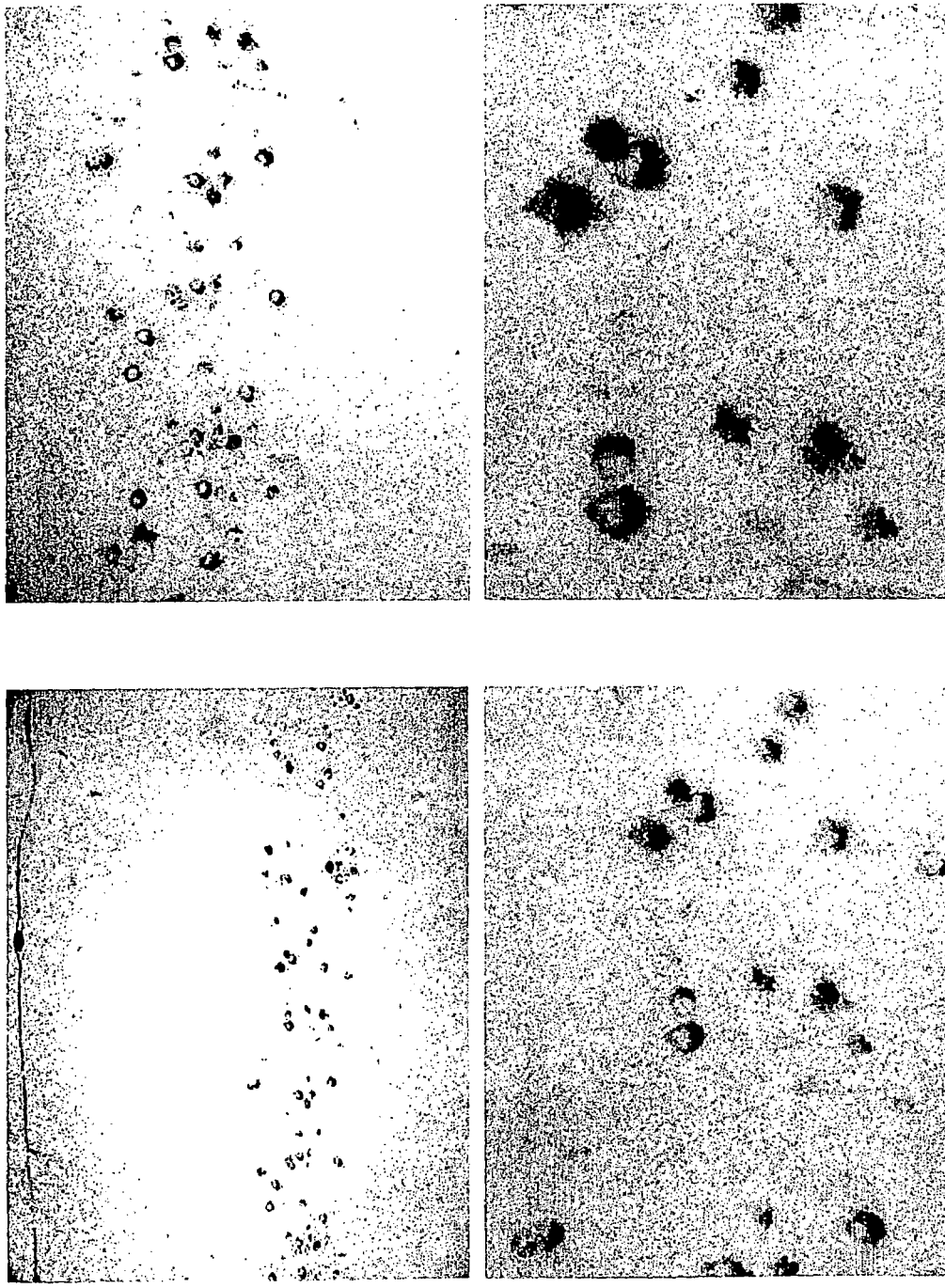
FIG. 10 is a photograph of brain sections taken from a triple transgenic mouse and stained with 6E10, an antibody specific for human APP protein. The black areas indicate another pathological alteration in the brains of triple transgenic mice; namely, Aβ deposition.

Brain sections from the triple transgenic B1 mice also exhibit Aβ deposition, a common feature in the brains of Alzheimer patients. In FIG. 10, brain sections from B1 transgenic mice stained with 6E10 antibody to human APP show Aβ deposition.

Example 5

Analysis of Steady-State Levels of Human Transgenes in 3×TL-AD Mice

Figure 11:
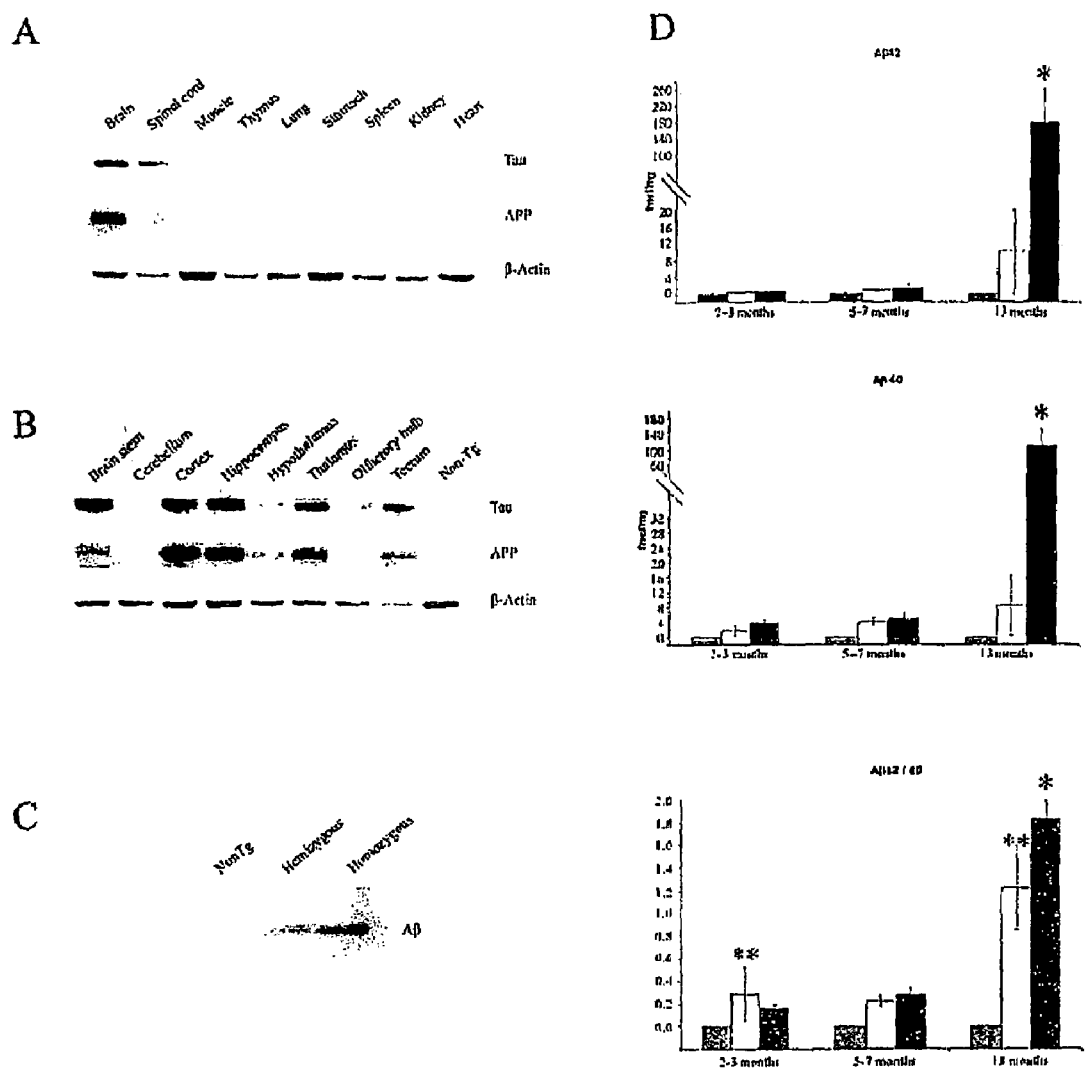
FIG. 11 shows an analysis of steady-state levels of the human transgenes in 3×Tg-AD mice. (A) Multiple peripheral tissues were surveyed by immunoblot analysis to determine the transgene expression profile. Tau and APP appear to be exclusively expressed in the central nervous system (CNS). (B) Quantitative comparison of transgene products in various brain subregions by western blotting. The hippocampus and cerebral cortex, two prominent AD-afflicted regions, are among the brain regions containing the highest steady-state levels of the human transgene products. (C) Aβ levels are doubled in the homozygous mice. Immunoprecipitation/western blotting shows that 4-KDa Aβ is detectable in the brains of both hemizygous and homozygous mice. (D) Aβ40 and Aβ42 levels measured by ELISA from different aged mice (n=3/group). Levels were measured as described previously (Parent, A., et al. (1999) Synaptic transmission and hippocampal long-term potentiation in transgenic mice expressing FAD-linked presenilin 1, *Neurobiol. Dis.* 6, 56-62). Non-transgenic (NonTg), hemizgyous and homozygous mice are depicted as blue, yellow, and red bars, respectively. Statistical difference between hemizygous and NonTg mice is denoted by **, whereas * indicates that homozygous mice are statistically different from hemizygous and NonTg mice.

The mouse Thy1.2 expression cassette has been demonstrated to drive transgene expression predominantly to the CNS (Caroni, P. (1997) Overexpression of growth-associated proteins in the neurons of adult transgenic mice, *J. Neurosci. Methods* 71, 3-9). Immunoblot analysis for human APP and tau in multiple peripheral tissues from the B1 3×Tg-AD line (the highest expressing line characterized) confirmed that expression was predominantly, if not exclusively, restricted to the CNS (FIG. 11A). To determine which regions of the CNS expressed the human APP and tau proteins, multiple brain regions (hippocampus, cortex, cerebellum, etc.) were microdissected, protein extracts were prepared and steady-state levels of the transgenic human proteins were measured by western blotting (FIG. 11B). As shown, the AD-relevant regions, including the hippocampus and cerebral cortex, were among the regions containing the highest steady-state levels of both the transgene-derived human APP and tau proteins. Other regions, such as the cerebellum, did not appear to contain any transgenic proteins, either because they are not expressed there or are rapidly degraded.

To determine whether the APP protein was processed to liberate the Aβ fragment, brain homogenates from hemizygous and homozygous mice were analyzed by immunoprecipitation/western blotting. FIG. 11C shows the presence of a 4-kDa species after probing with an Aβ-derived antibody that is twice as abundant in the homozygous versus the hemizygous brains, but undectectable in NonTg brain homogenates. Aβ40 and Aβ42 levels were also compared in the brains of age-and sex-matched NonTg and hemizygous and homozygous 3×Tg-AD mice by ELISA. There is a progressive increase in Aβ formation as a function of age in the 3×Tg-AD brains, and a particularly dramatic effect on Aβ42 levels (FIG. 11D).

Example 6

Aβ Deposition Precedes Tau Pathology in 3×Tg-AD Mice

Figure 12:
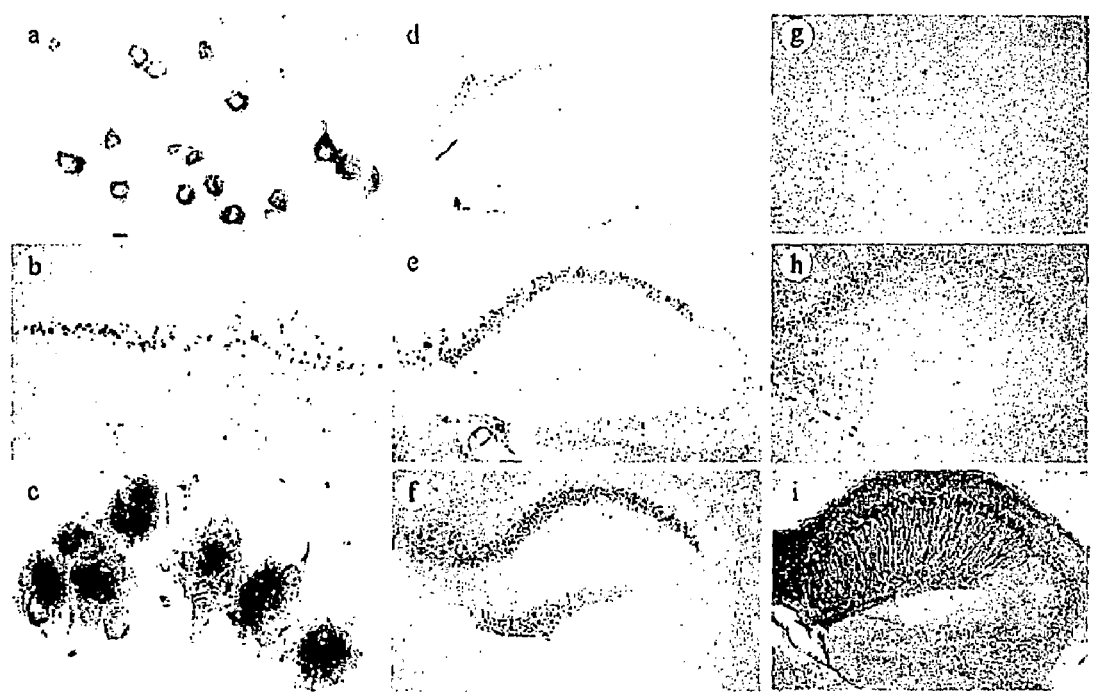
FIG. 12. Aβ deposition precedes tau pathology in 3×Tg-AD mice. (A) Aβ-immunoreactivity is first detected intracellularly in neurons within the neocortex. (B, C) Low and high magnification views, respectively, of the neocortex from a 9 month old homozygous mouse showing extracellular Aβ deposits in layer 4-5 of the neocortex. (D-F) Hippocampi of homozygous 3×Tg-AD mice (6, 12, 15 months old, respectively) showing first intraneuronal Aβ staining in the pyramidal neurons in the CA1 region (D) and then with extracellular Aβ staining (E,F). (G-I) Human tau immunoreactivity, detected with the human specific anti-tau antibody, HT7, is first apparent in the hippocampus and becomes more severe with advancing age (6, 12, 15 months old, respectively). Panels A-F show Aβ immunoreactivity using monoclonal antibody 6E10, panels G-I show tau immunostaining with antibody HT7. Original magnifications, 5× (D-I), 10× (B), 20× (A,C).

Intraneuronal Aβ immunoreactivity is one of the earliest neuropathological manifestations in the 3×Tg-AD mice, first detectable in neocortical regions, and subsequently in CA1 pyramidal neurons. Intracellular Aβ immunoreactivity is apparent between 3-4 months of age in the neocortex of 3×Tg-AD mice, and by 6 months of age in the CA1 subfield of the hippocampus of hemizygous and homozygous mice (FIG. 12A,D). This is followed by the emergence of extracellular Aβ deposits several months later (FIG. 12B,C). As with the intraneuronal staining, the largest cluster of extracellular Aβ deposits are first found in the frontal cortex and occur predominantly in layers 4-5, but involves other cortical layers and the hippocampus in older mice. By 12 months, extracellular Aβ deposits are readily apparent in other cortical regions, suggesting that there is an age-related, regional dependence to the Aβ deposits in the 3×Tg-AD mice that closely mimics the pattern found in the human AD brain. The progressive increase in Aβ deposition is corroborated by the ELISA data (FIG. 11D).

Because of the approach used to generate the 3×Tg-AD mice, both the tau and APP transgenes are expressed to comparable levels in the same brain regions. Consequently, these mice can be used to directly test the amyloid cascade hypothesis, which predicts that Aβ is the initiating trigger that underlies all cases of AD (Hardy, J. & Selkoe, D. J. (2002) The amyloid hypothesis of Alzheimer's disease: progress and problems on the road to therapeutics, *Science* 297,353-56). The development of Aβ and tau pathology in 3×Tg-AD mice, ranging in age from 6 to 15 months, was compared (cf FIG. 12*d-f* and 12*g-i*). Whereas intracellular Aβ immunoreactivity is present by 6 months of age in the hippocampus (and extracellular Aβ deposits in cortex), no significant tau immunoreactivity is present at this age (FIG. 12*g*). Human tau immunoreactivity is first evident at 12 months of age in the CA1 neurons, showing extensive immunolabeling of the somatodendritic compartments, and progressively more staining by 15 months (FIG. 12H,I).

Example 7

Tau Pathology Initiates in the Hippocampus and Progresses to the Neocortex

Figure 13:
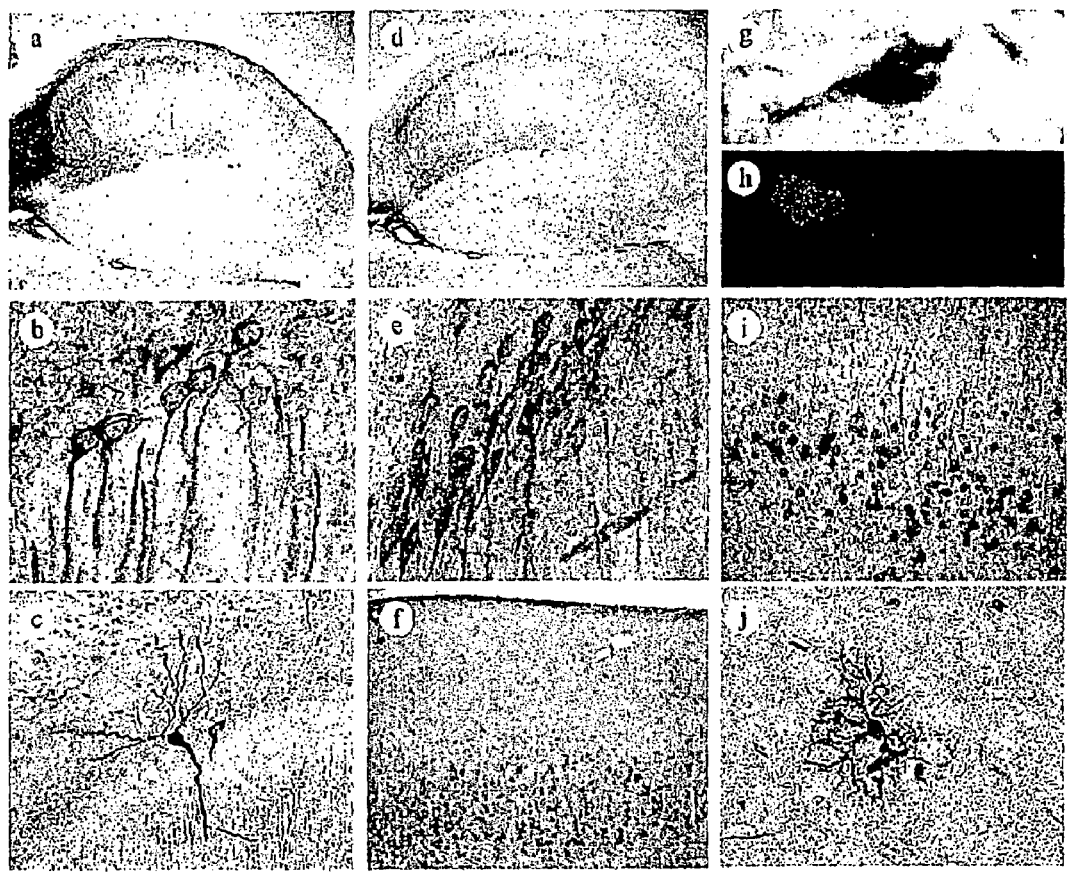
FIG. 13. Tau pathology initiates in the hippocampus and progresses to the neocortex. (A,B) Low and high magnification views of the hippocampus showing human tau immunopositive pyramidal neurons following staining with the conformational specific antibody MC1. (C) High magnification view showing immunopositive neurons following staining with antibody AT8, which detects phosphorylated tau proteins at serine 202 and threonine 205 residues. (D,E) Low and high magnification views of the hippocampus showing tau immunoreactive pyramidal neurons following staining with antibody AT180, which detects phosphorylated tau proteins at threonine 231 residues. (F) Immunostaining of neocortex with the human specific antibody HT7. (G,H) High magnification view of neocortical brain region from 12 month-old homozygous mice stained with Gallyas silver stain and thioflavin S. (I) High magnification view of the neocortex showing Aβ and tau co-localized to many of the same pyramidal neurons. Aβ was used immunostained with antibody 6E10 followed by detection with true blue (blue staining), whereas tau was immunostained with antibody HT7 and detected using DAB (brown staining). (J) GFAP immunoreactive astrocytes are also present around extracellular Aβ deposits. Original magnifications, 5× (A,D), 10× (P), 20× (C,I,J), 40× (B,E), 100× (G,H).

A subset of the neurons that are immunopositive for the human-specific tau antibody HT7 are also immunoreactive with several conformational-and phosphotau-specific antibodies. These include the conformation specific antibody MC1 (FIG. 13A,B), AT8, which detects tau phosphorylated at serine 202 and threonine 205 (FIG. 13C), and AT180, which detects phosphorylated tau at threonine 231 (FIG. 13D,E). As shown, tau is aberrantly hyperphosphorylated at multiple residues in the brains of the 3×Tg-AD mice. In contrast to the Aβ staining, tau immunostaining was first apparent in the CA1 region of the hippocampus and then progressively involved cortical neurons (FIG. 13F). Histological stains such as Gallayas and thioflavin S can also identify tau-reactive neurons (FIG. 13G,H). Finally, it is noted that reactive astrocytes were also readily apparent adjacent to extracellular Aβ deposits (FIG. 13J).

The 3×Tg-AD mice develop a progressive and age-dependent Aβ and tau pathology. The analysis presented herein indicates that Aβ pathology precedes tau pathology. As has been reported previously, it is likely that Aβ pathology affects the development of tau pathology (Lewis, J. et al. (2001) Enhanced neurofibrillary degeneration in transgenic mice expressing mutant tau and APP, *Science* 293, 1487-91; Gotz, J., et al. (2001) Formation of neurofibrillary tangles in P3011 tau transgenic mice induced by Aβ 42 fibrils, *Science* 293, 1491-5). Although Aβ and tau pathology initiate in different brain regions in the 3×Tg-AD mice (i.e., cortex for Aβ and hippocampus for tau), it is not inconsistent with the notion that Aβ influences tau pathology. The hypothesis that Aβ influences tau pathology is further supported by the finding that tau and Aβ immunoreactivity may be co-localized to the same neurons as revealed by double-labeling immunohistochemistry (FIG. 13I). Consequently, it is likely that intracellular Aβ immunoreactivity (which is the first detected pathological manifestation) affects the development of the tau pathology.

Example 8

Age Related Synaptic Dysfunction in 3×Tg-AD Mice

Neuronal and synaptic dysfunction are major phenotypic manifestations of AD neuropathology. Synaptic dysfunction, for example, is among the best correlates for the memory and cognitive changes that characterize AD. One-and six-month old homozygous 3×Tg-AD mice were compared to determine if there was an age-related impairment in synaptic functioning in the CA1 hippocampal region. Age-and sex-matched NonTg and PS1$_{M146V}$ KI mice were used as controls. PS1$_{M146V}$ KI mice were evaluated and used as controls because the electrophysiological properties of this line were unknown and because the 3xTg-AD mice were directly derived from this line. Thus it was crucial to determine the effect of the PS1 mutation on synaptic functioning. In addition, the 6-month time point was selected because extracellular Aβ deposits are evident only in the neocortex and not in the CA1 region of the hippocampus, although intracellular Aβ immunoreactivity is apparent. This allowed us to determine whether synaptic dysfunction precedes plaque and tau pathology in these nice.

To investigate basal synaptic transmission, input/output (I/O) curves were generated by measuring field excitatory postsynaptic potentials (fEPSPs) elicited in CA1 by stimulation of the Schaffer collaterals at increasing stimulus intensities. The I/O curves between one month PS1$_{M146V}$ KI and 3xTg-AD mice were not significantly different from NonTg mice (FIG. 14A). In contrast, 6 month PS1$_{M146V}$ KI and 3xTg-AD mice exhibited lesser fEPSP slopes and amplitudes at all stimulus intensities tested, and had significantly reduced maximum fEPSPs relative to NonTg mice (FIG. 14 B). The PS1$_{M146V}$ KI mice, however, were not significantly different from the 3xTg-AD mice (P<0.1). These results show that basal synaptic transmission is impaired in both the PS1$_{M146V}$ KI and 3xTg-AD mice at 6 months of age.

Paired-pulse facilitation (PPF), a measure of short-term plasticity, was also measured. No differences were observed in 1-month old PS1$_{M146V}$KI and 3xTg-AD mice (FIG. 14 C). At 6-months of age there was no difference in the amount of facilitation between NonTg and 3xTg-AD mice (NonTg, 31 ±1.5%; 3xTg-AD, 30±2.7%, P<0.5), but PS1$_{M146V}$ KI mice exhibited significantly enhanced PPF compared to NonTg mice (43±2.9%, P<0.01; FIG. 14D). The mechanisms underlying PPF are thought to be presynaptic (Zucker, R. S. & Regehr, W. G. (2002) Short-term synaptic plasticity, *Annu. Rev. Physiol.* 64, 355-405) and probably involve residual Ca$^{2+}$ in the nerve terminal after the first stimulus, leading to increased neurotransmitter release during the second stimulus (Thomson, A. M. (2002) Facilitation, augmentation and potentiation at central synapses, *Trends Neurosci.* 23, 305-12). The results shown herein suggest that presynaptic mechanisms are intact in 3xTg-AD mice, and the enhancement of facilitation in the PS1$_{M146V}$ KI mice may be due to alterations in handling intracellular Ca$^{2+}$ (Leissring, M. A. et al. (2000) Capacitative calcium entry deficits and elevated luminal calcium content in mutant presenilin-1 knockin mice, *J. Cell Biol.* 149, 793-8; LaFerla, F. M. (2002) Calcium dyshomeostasis and intracellular signaling in Alzheimer's disease (2002) *Nat. Reviews Neurosci.* 3, 862-872).

Long-term potentiation (LTP), a form of plasticity thought to underlie learning and memory (Bliss, T. V. & Collingridge, G. L. (1993) A synaptic model of memory: long-term potentiation in the hippocampus, *Nature* 361, 31-9), was investigated in the CA1 hippocampal region. No differences were observed between lines at 1-month of age (FIG. 14E). LTP in 6-month old 3xTg-AD mice was also investigated, and initial experiments showed that LTP was severely impaired in the 3xTg-AD mice. However, because the LTP induction protocol used a stimulus intensity that elicited ~30% of the maximum fEPSP slope during baseline and high frequency stimulation (HFS), it is plausible that the smaller absolute fEPSP may account for the LTP deficits.

To address this possibility, the stimulus intensity was adjusted to match baseline fEPSP magnitudes to those of NonTg mice. LTP magnitudes in these experiments did not significantly differ when weaker stimulus intensities were used (data not shown), indicating that reduced basal transmission does not likely account for the deficits in LTP, although a ceiling affect cannot be discounted. All the data from the 3xTg-AD mice was subsequently pooled and demonstrated reduced LTP (FIG. 14F). In contrast, LTP in the PS1$_{M146V}$KI mice was essentially normal and did not differ from NonTg mice 50-60 minutes after HFS, despite weaker fEPSPs relative to NonTg controls. There was, however, a trend in the PS1$_{M146V}$KI mice for significantly higher LTP during the first 10 minutes after HFS, as has also been reported in the transgenic mice overexpressing PS1$_{A246E}$ variant (Parent, A., supra). As with the 3xTg-AD mice, raising baseline fEPSPs to NonTg levels did not result in significantly different LTP magnitude and thus the data were pooled.

These results show that the 3xTg-AD mice exhibit deficits in basal synaptic transmission and LTP with the appearance of intracellular All but prior to the formation of extracellular plaques and tau pathology. In contrast, the PS1$_{M146V}$KI mice demonstrated normal-to-enhanced LTP, despite deficits in basal synaptic transmission, suggesting that the mechanisms underlying the transmission and LTP deficits in the 3xTg-AD mice may be independent. All the groups compared in these studies have the same genetic background, which helps analysis considerably as LTP can be markedly affected in different inbred mouse strains (Nguyen, P. V., et al. (2000) Strain-dependent differences in LTP and hippocampus-dependent memory in inbred mice, *Learn. Mem.* 7, 170-9). The subsequent characterization of synaptic dysfunction in these two models (i.e., 3xTg-AD and PS1$_{M146V}$ KI) will help resolve the underlying mechanisms involved and the contribution of the different gene mutations that have been implicated in AD. In addition, future studies will help discern the relationship that Aβ and tau pathology exert on synaptic function.

A novel strategy to develop multi-transgenic animals, and in particular a triple transgenic model of AD, has been disclosed herein. Compared to cross-breeding, this approach has several major advantages. The APP and tau transgenes cointegrated at the same genetic locus, rendering it unlikely that either transgene will independently assort in subsequent generations. Consequently, this tight linkage coupled to the 'knockin' of the PS1 mutation indicates that the 3xTg-AD mice breed as readily as any single transgenic line, particularly since these mice have also been bred to homozygosity. Thus, deriving large numbers of these 3xTg-AD mice is straightforward and cost-effective. Moreover, the easy maintenance of this transgenic line facilitates the crossing of these 3xTg-AD mice to other transgenic or gene-targeted mice. Finally, another major advantage with this approach is that multiple transgenes are introduced into an animal without altering or mixing the background genetic constitution. Thus, an important confounding variable is avoided, which may be a crucial issue for behavioral, electrophysiological, and vaccine-based experiments.

As shown, 3xTg-AD mice develop an age-related and progressive neuropathological phenotype that is more robust in the homozygous mice. Intracellular Aβ immunoreactivity is the first clear neuropathological manifestation in the brains of these transgenic mice. There is evidence that intracellular Aβ deposition may be important in the pathogenesis of AD (LaFerla, F. M., et al. (1997) Neuronal cell death in Alzheimer's disease correlates with apoE uptake and intracellular Aβ stabilization, *J. Clin. Invest.* 100, 310-20; Gouras, G. K et al. (2000) Intraneuronal Aβ42 accumulation in human brain, *Am. J. Pathol.* 156, 15-20) and in the related disorder inclusion body myositis (Sugarman, M. C. et al. (2002) Inclusion body myositis-like phenotype induced by transgenic overexpression of βAPP in skeletal muscle, *Proc. Natl. Acad. Sci. U.S.A.* 99, 6334-9; Mendell, J. R., et al. (1991) Amyloid filaments in inclusion body myositis: Novel findings provide insight into nature of filaments, *Arch. Neurol.* 48, 1229-34). Intraneuronal Aβ has also been documented in the brains of other AD transgenic mouse models (Wirths, O. et al. (2001) Intraneuronal Aβ accumulation precedes plaque formation in beta-amyloid precursor protein and presenilin-1 double-transgenic mice, *Neurosci. Lett.* 306, 116-20; Li, Q. X. et al. (1999) Intracellular accumulation of detergent-soluble amyloidogenic Aβ fragment of Alzheimer's disease precursor protein in the hippocampus of aged transgenic mice, *J. Neurocheni.* 72, 2479-87; Kuo, Y. M. et al. (2001) The evolution of Aβ peptide burden in the APP23 transgenic mice: implications for Aβ deposition in Alzheimer disease, *Mol. Med.* 7, 609-18; LaFerla, F. M., et al. (1995) The Alzheimer's Aβ peptide induces neurodegeneration and apoptotic cell death in transgenic mice, *Nat. Genet.* 9, 21-30). The pathophysiological relevance of intraneuronal Aβ, however, is not yet resolved, although it is tempting to speculate that it maybe the source of the extracellular Aβ deposits. Herein it is shown that the occurrence of intraneuronal Aβ in CA1 pyramidal neurons correlates with impairments in synaptic transmission, including deficits in LTP. The finding that synaptic transmission and LTP deficits precede overt plaque and tau pathology suggests that synaptic dysfunction is an early manifestation of AD. Furthermore, these studies indicate that extracellular Aβ deposition is not the causal factor underlying the synaptic dysfunction. This agrees well with recent findings that show that soluble Aβ oligomers inhibit LTP in vivo (Walsh, D. M. et al. (2002) Naturally secreted oligomers of amyloid beta protein potently inhibit hippocampal long-term potentiation in vivo, *Nature* 416, 535-9).

It is also shown herein that Aβ pathology precedes tau pathology in this model. Because the APP and tau transgenes were expressed to comparable levels, this observation provides strong experimental support for the amyloid cascade hypothesis. This hypothesis posits that Aβ accumulation, which may occur as a consequence of overproduction, mismetabolism, or failures in clearance, is the initiating trigger that underlies all forms of AD. The development of both Aβ and tau pathology in the 3×Tg-AD mouse model is significant as it should enable a more accurate evaluation of potential therapeutic interventions (such as Aβ immunizations) in an animal model that more closely mimics the neuropathology of AD. In addition, this model will be useful for determining if modulation of either the Aβ or tau pathology impacts the development of the other.

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. In particular, it is to be understood that this invention is not limited to the particular methodology, protocols, cell lines, animal species or genera, constructs, and reagents described as such may vary, as will be appreciated by one of skill in the art. The scope of the invention is, therefore, indicated by the following claims rather than by the foregoing description. All changes, modifications, and variations coming within the meaning and range of equivalency of the claims are to be considered within their scope.

What is claimed is:

1. A triple transgenic mouse whose genome comprises:
    a knock-in first transgene encoding a mutant human presenilin-1 polypeptide having a mutation associated with Alzheimer's disease (AD) or AD-type pathology;
    a second transgene, encoding mutant human Tau protein having a mutation associated with AD or AD-type pathology operably linked to a promoter; and
    a third transgene, encoding human β-amyloid precursor protein (βAPP) having a mutation associated with AD or AD-type pathology operably linked to a promoter,
    wherein expression of the transgenes results in a Tau pathology in the triple transgenic mouse.

2. The transgenic mouse of claim 1, wherein the mouse is fertile and transmits the three transgenes to its offspring.

3. The transgenic mouse of claim 1, wherein the second and third transgenes have been introduced into an ancestor of said mouse at an embryonic stage.

4. The transgenic mouse of claim 1, wherein the mouse is hemizygous for the human βAPP transgene.

5. The transgenic mouse of claim 1, wherein the mouse is homozygous for the human βAPP transgene.

6. The transgenic mouse of claim 1, wherein the mouse is hemizygous for the human tau transgene.

7. The transgenic mouse of claim 1, wherein the mouse is homozygous for the human tau transgene.

8. The triple transgenic mouse claim 1, wherein the second and third transgenes co-integrate at the same genetic locus.

9. The triple transgenic mouse claim 1, wherein the second and third transgenes encode Tau P301 L and APP SWE, respectively.

10. The triple transgenic mouse claim 1, wherein the promoter is a Thy1.2 promoter.

11. A triple transgenic mouse-whose genome comprises:
    a knock-in first transgene encoding mutant human presenilin-1 polypeptide having a mutation associated with Alzheimer's disease (AD) or AD-type pathology;
    a second transgene, encoding mutant human Tau protein having a mutation associated with AD or AD-type pathology operably linked to a promoter; and
    a third transgene, encoding human β-amyloid precursor protein (βAPP) having a mutation associated with AD or AD-type pathology operably linked to a promoter,
    wherein expression of the transgenes results in a Aβ pathology in the triple transgenic mouse.

12. The transgenic mouse of claim 11, wherein the mouse is fertile and transmits the three transgenes to its offspring.

13. The transgenic mouse of claim 11, wherein the second and third transgenes have been introduced into an ancestor of said mouse at an embryonic stage.

14. The transgenic mouse of claim 11, wherein the mouse is hemizygous for the human βAPP transgene.

15. The transgenic mouse of claim 11, wherein the mouse is homozygous for the human βAPP transgene.

16. The transgenic mouse of claim 11, wherein the mouse is hemizygous for the human tau transgene.

17. The transgenic mouse of claim 11, wherein the mouse is homozygous for the human tau transgene.

18. The triple transgenic mouse claim 11, wherein the second and third transgenes co-integrate at the same genetic locus.

19. The triple transgenic mouse claim 11, wherein the second and third transgenes encode Tau P301 L and APP SWE, respectively.

20. The triple transgenic mouse claim 11, wherein the promoter is a Thy1.2 promoter.

21. A method for making a multi-transgenic mouse the method comprising:
providing a knock-in mouse whose genome comprises a knock-in first transgene that encodes a mutant human presenilin-1;
cross-breeding said transgenic mouse with a second knock-in mouse transgenic for said first transgene to obtain an embryo homozygous for said first transgene;
microinjecting a second transgene into said homozygous embryo, wherein the second transgene is selected from the group consisting of a transgene encoding mutant Tau or a transgenic encoding mutant APP each mutant associated with Alzheimer's disease (AD) or AD-type pathology and each transgene is operably linked to a promoter; and
allowing the embryo to develop to term to produce a multi-transgenic mouse whose genome comprises the two transgenes.

22. The method of claim 21, further comprising the step of microinjecting a third transgene into the embryo, wherein said second and third transgenes encode between them both mutant Tau or mutant APP each mutant associated with Alzheimer's disease (AD) or AD-type pathology and each transgene is operably linked to a promoter, to produce a mouse whose genome comprises the three transgenes.

23. The method of claim 22, wherein the second and third transgenes co-integrate at the same genetic locus.

24. The method of claim 22, wherein the second and third transgenes encode Tau P301 L and APP SWE, respectively.

25. The method of claim 22, wherein the promoter is a Thy1.2 promoter.

26. A method for making a triple transgenic mouse, the method comprising:
providing a mouse whose genome comprises a knock-in first transgene encoding a mutant presenilin-1;
cross-breeding said transgenic mouse with a second mouse whose genome also comprises said first transgene to obtain an embryo homozygous for said first transgene;
co-microinjecting a second transgene and a third transgene into said homozygous embryo, wherein said second and third transgenes encode either a mutant Tau or a mutant APP associated with Alzheimer's disease (AD) or AD-type pathology, and wherein each transgene is operably linked to a promoter; and allowing the embryo to develop to term to produce a triple transgenic mouse whose genome comprises the three transgenes.

27. The method of claim 26, wherein the second and third transgenes co-integrate at the same genetic locus.

28. The method of claim 26, wherein the second and third transgenes encode Tau P301 L and APP SWE, respectively.

29. The method of claim 26, wherein the promoter is a Thy1.2 promoter.

30. A multi-transgenic mouse produced by the steps of:
providing a knock-in mouse whose genome comprises a knock-in first transgene that encodes mutant human presenilin-1;
cross-breeding said transgenic mouse with a second knock-in mouse transgenic for said first transgene to obtain an embryo homozygous for said first transgene;
microinjecting a second transgene into said homozygous embryo, wherein the second transgene is selected from the group consisting of a transgene encoding mutant Tau or a transgenic encoding mutant APP each mutant associated with Alzheimer's disease (AD) or AD-type pathology and each transgene is operably linked to a promoter; and
allowing the embryo to develop to term to produce a multi-transgenic mouse whose genome comprises the two transgenes.

31. A triple transgenic mouse, produced by the steps of:
providing a mouse whose genome comprises a knock-in first transgene encoding a mutant presenilin-1;
cross-breeding said transgenic mouse with a second mouse whose genome also comprises said first transgene to obtain an embryo homozygous for said first transgene;
co-microinjecting a second transgene and a third transgene into said homozygous embryo, wherein said second and third transgenes encode either a mutant Tau or a mutant APP associated with Alzheimer's disease (AD) or AD-type pathology, and wherein the transgenes are operably linked to a promoter; and
allowing the embryo to develop to term to produce a triple transgenic mouse whose genome comprises the three transgenes,
wherein expression of the transgenes results in the deposition of Aβ in the brain of the mouse.

32. The triple transgenic mouse claim 31, wherein the second and third transgenes co-integrate at the same genetic locus.

33. The triple transgenic mouse claim 31, wherein the second and third transgenes encode Tau P301 L and APP SWE, respectively.

34. The triple transgenic mouse claim 31, wherein the promoter is a Thy1.2 promoter.

35. A triple transgenic mouse whose genome comprises:
a knock-in first transgene encoding a mutant human presenilin-1 polypeptide having a mutation associated with Alzheimer's disease (AD) or AD-type pathology;
a second transgene, encoding mutant human Tau protein having a mutation associated with AD or AD-type pathology operably linked to a promoter; and
a third transgene, encoding human β-amyloid precursor protein (βAPP) having a mutation associated with AD or AD-type pathology operably linked to a promoter,
wherein expression of the transgenes results in a Tau pathology and an Aβ pathology in the triple transgenic mouse.

36. The triple transgenic mouse claim 35, wherein the second and third transgenes co-integrate at the same genetic locus.

37. The triple transgenic mouse claim 35, wherein the second and third transgenes encode Tau P301 L and APP SWE, respectively.

38. The triple transgenic mouse claim 35, wherein the promoter is a Thy1.2 promoter.

39. A triple transgenic mouse whose genome comprises:
a knock-in first transgene encoding a mutant human presenilin-1 polypeptide having a mutation associated with Alzheimer's disease (AD) or AD-type pathology;
a second transgene, encoding mutant human Tau protein having a mutation associated with AD or AD-type pathology operably linked to a promoter; and
a third transgene, encoding human β-amyloid precursor protein (βAPP) having a mutation associated with AD or AD-type pathology operably linked to a promoter,
wherein expression of the transgenes results in an AD or AD-type pathology in the triple transgenic mouse.

40. The triple transgenic mouse claim 39, wherein the second and third transgenes co-integrate at the same genetic locus.

41. The triple transgenic mouse claim 39, wherein the second and third transgenes encode Tau P301 L and APP SWE, respectively.

42. The triple transgenic mouse claim 39, wherein the promoter is a Thy1.2 promoter.

43. A method of screening for biologically active agents that facilitate reduction of a tau pathology in vivo, the method comprising:
   administering a candidate agent to a transgenic mouse according to claim 1, and determining the effect of said agent on the Tau pathology.

44. A method of screening for biologically active agents that facilitate reduction of an Aβ pathology in vivo, the method comprising:
   administering a candidate agent to a transgenic mouse according to claim 11, and determining the effect of said agent on the Aβ pathology.

45. A method of screening for biologically active agents that facilitate reduction in both Tau pathology and Aβ pathology in vivo, the method comprising:
   administering a candidate agent to a transgenic mouse according to claim 35, and determining the effect of said agent on both Tau pathology and Aβ pathology.

46. A method of screening for biologically active agents that facilitate reduction in AD or AD-type pathology in vivo, the method comprising:
   administering a candidate agent to a transgenic mouse according to claim 39, and determining the effect of said agent on the AD or AD-type pathology.

* * * * *

UNITED STATES PATENT AND TRADEMARK OFFICE
CERTIFICATE OF CORRECTION

PATENT NO.        : 7,479,579 B2                                                        Page 1 of 1
APPLICATION NO.   : 10/499269
DATED             : January 20, 2009
INVENTOR(S)       : Frank M. LaFerla It is certified that error appears in the above-identified patent and that said Letters Patent is hereby corrected as shown below:

In column 24, line 2, of claim 45, after pathology and delete "A13" and insert --AB--.

Signed and Sealed this

First Day of June, 2010

David J. Kappos
*Director of the United States Patent and Trademark Office*